(12) United States Patent
Jepson et al.

(10) Patent No.: US 12,045,905 B2
(45) Date of Patent: *Jul. 23, 2024

(54) SYSTEMS AND METHODS FOR TRANSPORTATION COORDINATION IN HEALTHCARE AND OTHER SETTINGS

(71) Applicant: Hitch Health, Inc., Wayzata, MN (US)

(72) Inventors: Susan Funk Jepson, Minnetonka, MN (US); Charles Loeb Truwit, Wayzata, MN (US)

(73) Assignee: Hitch Health, Inc., Wayzata, MN (US)

( * ) Notice: Subject to any disclaimer, the term of this patent is extended or adjusted under 35 U.S.C. 154(b) by 338 days.

This patent is subject to a terminal disclaimer.

(21) Appl. No.: 17/444,816

(22) Filed: Aug. 10, 2021

(65) Prior Publication Data

US 2021/0374893 A1     Dec. 2, 2021

Related U.S. Application Data

(63) Continuation of application No. 15/850,304, filed on Dec. 21, 2017, now Pat. No. 11,087,423.

(60) Provisional application No. 62/437,485, filed on Dec. 21, 2016.

(51) Int. Cl.
    *G06Q 50/40*      (2024.01)
    *G06Q 10/1093*      (2023.01)
    *G06Q 20/10*      (2012.01)
    *G16H 10/60*      (2018.01)
    *G16H 40/20*      (2018.01)
    *H04W 4/12*      (2009.01)

(52) U.S. Cl.
CPC ......... *G06Q 50/40* (2024.01); *G06Q 10/1095* (2013.01); *G06Q 20/102* (2013.01); *G16H 10/60* (2018.01); *G16H 40/20* (2018.01); *H04W 4/12* (2013.01)

(58) Field of Classification Search
CPC ..... G06Q 50/30; G06Q 10/1095; G16H 40/20
See application file for complete search history.

(56) References Cited

U.S. PATENT DOCUMENTS

| | | | | |
|---|---|---|---|---|
| 2005/0038696 | A1* | 2/2005 | Kalevik | G06Q 10/08 705/13 |
| 2013/0185221 | A1* | 7/2013 | Adams | G06Q 50/30 705/333 |
| 2015/0046187 | A1* | 2/2015 | Johnson | G06Q 50/30 705/3 |
| 2016/0063658 | A1* | 3/2016 | Breazeale, Jr. | G16H 15/00 705/2 |
| 2016/0364824 | A1* | 12/2016 | Bryant | G06Q 10/063114 |
| 2018/0204157 | A1* | 7/2018 | Li | G08G 1/202 |

* cited by examiner

*Primary Examiner* — Sheetal R Paulson
(74) *Attorney, Agent, or Firm* — Pranger Law PC

(57) ABSTRACT

Embodiments relate to systems and methods for coordinating, arranging and/or managing transportation. These systems and methods can be used and applied in a variety of settings and industries, including healthcare, travel, hospitality, event, dining and entertainment, and others.

22 Claims, 38 Drawing Sheets

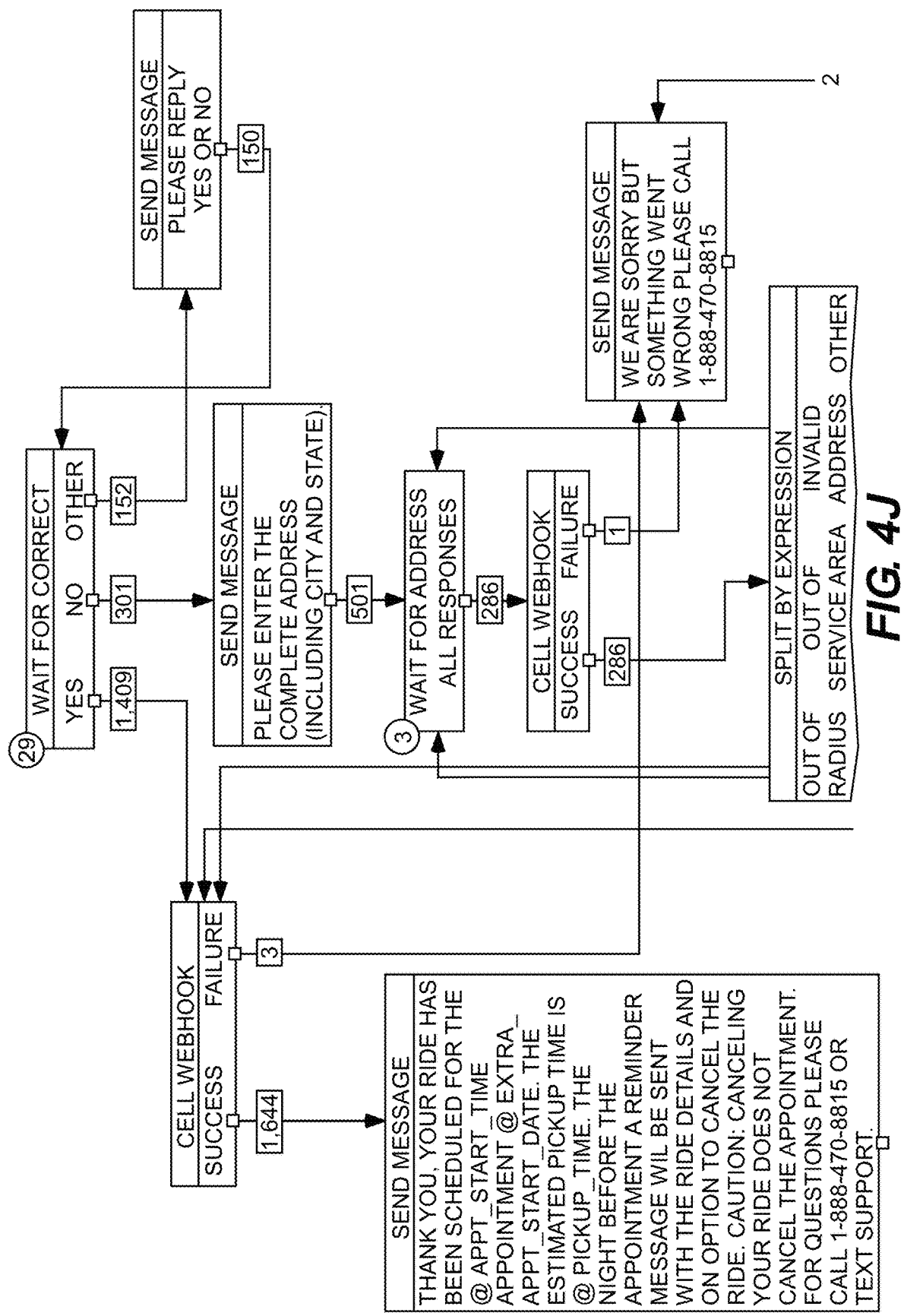

HITCH+

Whittier Clinic
2810 Nicollet Ave.
Minneapolis, MN 55400

[Sign Out] [Request A Ride]

For issues contact 612-555-4363

| Cancer (2) | Cardiology | Psychiatric |

[December ▼] [13 (2016) ▼] [View]

Arrivals | Departures | Completed | Canceled (2)

| Patient Status | ETA ⇅ | Appt ⇅ | Patient Name ⇅ | Patient ID ⇅ | Mobile Phone | Home Address |
|---|---|---|---|---|---|---|
| ✓ Dropped Off | 8:15AM | 8:00AM | Travis B. | 12345677 | (612) 454-4456 | 110 North 5th Street, Minneapolis, MN |
| Dropped Off  Destination: Blue Zone  Time: 9:05AM  Duration: 0:20:32  Driver: Mark M.  Toyota Camry  MJK-445  (555)444-5057 | | | | | | |
| ⇨ In Transit | 8:22AM | 8:15AM | Alexandria J. | 12345677 | (612) 454-4456 | 110 North 5th Street, Minneapolis, MN |
| ⇨ In Transit | 8:25AM | 9:15AM | Patrick H. | 12345677 | (612) 454-4456 | 110 North 5th Street, Minneapolis, MN |
| ↻ Awaiting Pickup | --- | 9:00AM | Ramona S. | 12345677 | (612) 454-4456 | 110 North 5th Street, Minneapolis, MN |
| ↻ Awaiting Pickup | --- | 9:00AM | Callum D. | 12345677 | (612) 454-4456 | 110 North 5th Street, Minneapolis, MN |
| Requesting | --- | 9:45AM | Cecil K. | 12345677 | (612) 454-4456 | 110 North 5th Street, Minneapolis, MN |
| Reserved | --- | 10:00AM | Anna R. | 12345677 | (612) 454-4456 | 110 North 5th Street, Minneapolis, MN |
| ✗ Canceled | --- | 10:30AM | Anna R. | 12345677 | (612) 454-4456 | 110 North 5th Street, Minneapolis, MN |

Additional Dropdown Views

In Transit  Destination: Blue Zone  Driver: Mark M.  Toyota Camry  MJK-445  (555)444-5647

Waiting for Patient  Destination: Blue Zone  Driver: Mark M.  Toyota Camry  MJK-445  (555)444-5647

Canceled by Patient  Destination: Blue Zone  Time: 9:05AM  Driver: Mark M.  Toyota Camry  MJK-445  (555)444-5647

Canceled by Driver (No Show)  Destination: Blue Zone  Time: 9:05AM  Driver: Mark M.  Toyota Camry  MJK-445  (555)444-5647

*FIG. 8A*

HITCH+

Whittier Clinic
2810 Nicollet Ave.
Minneapolis, MN 55400

[Sign Out]  [Request A Ride]

For issues contact 612-555-4363

Cancer (2) | Cardiology | Psychiatric

Arrivals | Departures | Completed | Canceled (2)

December ▼ | 13 (2018) ▼ | View

| Patient Status | Pickup | Patient Name ⇅ | Patient ID ⇅ | Mobile Phone | Home Address |
|---|---|---|---|---|---|
| ✓ Dropped Off | Blue | Travis B. | 12345677 | (612) 454-4456 | 110 North 5th Street, Minneapolis, MN |
| ⇨ In Transit | Blue | Alexandria J. | 12345677 | (612) 454-4456 | 110 North 5th Street, Minneapolis, MN |
| ⇨ In Transit | Blue | Patrick H. | 12345677 | (612) 454-4456 | 110 North 5th Street, Minneapolis, MN |
| ↻ Awaiting Pickup | Green | Ramona S. | 12345677 | (612) 454-4456 | 110 North 5th Street, Minneapolis, MN |
| ↻ Awaiting Pickup | Blue | Callum D. | 12345677 | (612) 454-4456 | 110 North 5th Street, Minneapolis, MN |
|   Requesting | Blue | Cecil K. | 12345677 | (612) 454-4456 | 110 North 5th Street, Minneapolis, MN |
|   Reserved | Blue | Anna R. | 12345677 | (612) 454-4456 | 110 North 5th Street, Minneapolis, MN |
| ✗ Canceled | Blue | Anna R. | 12345677 | (612) 454-4456 | 110 North 5th Street, Minneapolis, MN |

Additional Dropdown Views

In Transit  Destination: Home  Driver: Mark M.  Toyota Camry  MJK-445  (555)444-5647

Waiting for Patient  Destination: Home  Driver: Mark M.  Toyota Camry  MJK-445  (555)444-5647

Canceled by Patient  Destination: Home  Time: 9:05AM  Driver: Mark M.  Toyota Camry  MJK-445  (555)444-5647

Canceled by Driver (No Show) Destination: Home  Time: 9:05AM  Driver: Mark M.  Toyota Camry  MJK-445  (555)444-5647

*FIG. 8B*

HITCH+

Whittier Clinic
2810 Nicollet Ave.
Minneapolis, MN 55400

[Sign Out] [Request A Ride]

For issues contact 612-555-4363

| | Cancer (2) | Cardiology | Psychiatric |

Arrivals | Departures | Completed | Canceled (2)

[December ▾] [13 (2016) ▾] [View]

| Location | | Time ⇅ | Duration ⇅ | Patient Name ⇅ | Patient ID ⇅ | Mobile Phone | Home Address |
|---|---|---|---|---|---|---|---|
| ♡ | HCMC | 9:15AM | 0:28:32 | Travis B. | 12345677 | (612) 454-4456 | 110 North 5th Street, Minneapolis, MN |
| ⌂ | Home | 8:22AM | 0:44:12 | Alexandria J. | 12345677 | (612) 454-4456 | 110 North 5th Street, Minneapolis, MN |
| ⌂ | Home | 8:25AM | 0:18:36 | Patrick H. | 12345677 | (612) 454-4456 | 110 North 5th Street, Minneapolis, MN |
| ♡ | HCMC | 8:25AM | 1:12:22 | Ramona S. | 12345677 | (612) 454-4456 | 110 North 5th Street, Minneapolis, MN |
| ♡ | HCMC | 8:45AM | 0:22:33 | Callum D. | 12345677 | (612) 454-4456 | 110 North 5th Street, Minneapolis, MN |
| ♡ | HCMC | 9:00AM | 0:52:11 | Cecil K. | 12345677 | (612) 454-4456 | 110 North 5th Street, Minneapolis, MN |
| ♡ | HCMC | 9:00AM | 0:39:33 | Anna R. | 12345677 | (612) 454-4456 | 110 North 5th Street, Minneapolis, MN |
| ⌂ | Home | 9:15AM | 0:28:34 | Anna R. | 12345677 | (612) 454-4456 | 110 North 5th Street, Minneapolis, MN |

Additional Dropdown Views

Dropped Off   Destination: Blue Zone   Pickup: Home   Driver: Mark M.   Toyota Camry   MJK-445   (555)444-5647

Dropped Off   Destination: Home   Pickup: Blue Zone   Destination: 0:26:32   Driver: Mark M.   Toyota Camry   MJK-445   (555)444-5647

*FIG. 8C*

HITCH+

Whittier Clinic
2810 Nicollet Ave.
Minneapolis, MN 55400

Sign Out | Request A Ride

For issues contact 612-555-4363

Cancer (2) | Cardiology | Psychiatric

Arrivals | Departures | Completed | Canceled (2)

December ▼ | 13 (2016) ▼ | View

| Initiated By | Time | Patient Name | Patient ID | Mobile Phone | Home Address |
|---|---|---|---|---|---|
| ✕ Lyft | 8:15AM | Anna R. | 12345677 | (612) 454-4456 | 110 North 5th Street, Minneapolis, MN |
| ✕ Patient | 9:05AM | Anna R. | 12345677 | (612) 454-4456 | 110 North 5th Street, Minneapolis, MN |
| Staff | 10:15AM | Anna R. | 12345677 | (612) 454-4456 | 110 North 5th Street, Minneapolis, MN |
| System | 2:45PM | Anna R. | 12345677 | (612) 454-4456 | 110 North 5th Street, Minneapolis, MN |

Additional Dropdown Views

| Canceled by Customer | Destination: Home | Time: 9:05AM | Driver: Mark M. | Toyota Camry | MJK-445 | (555)444-5647 |

| Canceled by Driver (No Show) | Destination: Home | Time: 9:05AM | Driver: Mark M. | Toyota Camry | MJK-445 | (555)444-5647 |

| Canceled by Staff (John G.) | Destination: Home | Time: 9:05AM | Driver: Mark M. | Toyota Camry | MJK-445 | (555)444-5647 |

| Canceled by System (Invalid Address) | Destination: Home | Time: 9:05AM |

HITCH+

Whittier Clinic
2810 Nicollet Ave.
Minneapolis, MN 55400

Sign Out | Request A Ride

For issues contact 612-555-4363

Please be aware that this request will immediately dispatch a car for the patient.

Select Pickup Location
○ [Green]
◉ [Blue]

Patient ID
[          ]

— or —

Patient First Name
[               ]

Patient Mobile Number
[          ]

Home Street Address
[ Street Address only ]

City
[ Select a City ▼ ]

[ Request Ride ]

| HITCH+ | [Arrivals] Departures Request a Ride Appointments Patients CSV Upload Reports | HCMC Admin (HA) |

Whittler Clinic
November 7, 2017

There are 24 rides scheduled for today.
Updated as of: 10:15AM

*For Technical Support:* email
SupportStaff@hcmed.org

[All Departments ▼] [2017-11-07] [Search by Mobile Phone 🔍] ✕

<< November 6, 2017                                                                 November 8, 2017 >>

Appointment Times

9AM  9:00 | 9:15 | 9:30 | 9:45
- DROPPED OFF Allene H. ✓
- No scheduled rides
- No scheduled rides
- No scheduled rides Appointment Times

10AM  10:00 | 10:15 | 10:30 | 10:45
- No scheduled rides
- No scheduled rides
- No scheduled rides
- No scheduled rides Appointment Times

11AM  11:00 | 11:15 | 11:30 | 11:45
- DROPPED OFF Claudine D. ✓
- DROPPED OFF Ima B. ✓
- No scheduled rides
- No scheduled rides
- CANCELED BY PASSENGER Loraine B. ✕

| HITCH | Arrivals ┆Departures┆ Request a Ride  Appointments  Patients  CSV Upload  Reports | HCMC Admin (HA) |

Whittler Clinic  
November 7, 2017

There are 1 rides scheduled for today.  
Updated as of: 10:19AM

For Technical Support: email  
SupportStaff@hcmed.org

[ All Departments ▼ ] [ 2017-11-07 ] [ Search by Mobile Phone 🔍 ] ✕

<< November 8, 2017                                                                 November 8, 2017 >>

8AM    | PICKED UP
         Allene H.                                          ✓ |

9AM    | No departures scheduled |

| | | | | | | | | | |
|---|---|---|---|---|---|---|---|---|---|
| HITCH+ | Arrivals | Departures | Request a Ride | Appointments Reports | Patients | CSV Upload | | HCMC Admin | HA |

Appointments      Search by Mobile Phone 🔍 ✕

| Unique ID | Status | Patient | Mobile Phone | Department | Address | Patient Pickup | Start Time | Health System | Ride Scheduled | Msgs |
|---|---|---|---|---|---|---|---|---|---|---|
| T71D8Q47 | Scheduled | Charlie P. | (335) 555-2638 | | Whittier Entrance 2810 Nicollet Avenue Minneapolis, MN 55408 | Suite 197, 112 Brown Ridge Edina, MN 55207 | 11/13/17 06:20 PM | HCMC | Yes (reserved) | View |
| FR73SP9Z | Scheduled | Bradley C. | (417) 555-6597 | | Whittier Entrance 2810 Nicollet Avenue Minneapolis, MN 55408 | Apt. 176, 38470 Reynolds Pine Richfield, MN 55604 | 11/13/17 08:00 PM | HCMC | Yes (reserved) | View |
| LDG52AJ0 | Scheduled | Daryl H. | (627) 555-6841 | | Whittier Entrance 2810 Nicollet Avenue Minneapolis, MN 55408 | Apt. 989, 32582 Roselyn Glens Edina, MN 55439 | 11/13/17 07:40 PM | HCMC | Yes (reserved) | View |
| UICE6PB0 | Scheduled | Bud S. | (186) 555-1024 | | Whittier Entrance 2810 Nicollet Avenue Minneapolis, MN 55408 | Suite 822, 498 Hansen Crossroad Richfield, MN 55155 | 11/13/17 07:40 PM | HCMC | Yes (reserved) | View |

SYSTEMS AND METHODS FOR TRANSPORTATION COORDINATION IN HEALTHCARE AND OTHER SETTINGS

RELATED APPLICATION

This application is a continuation of application Ser. No. 15/850,304 filed Dec. 21, 2017, which claims the benefit of U.S. Provisional Application No. 62/437,485, filed Dec. 21, 2016, each of which is hereby fully incorporated herein by reference.

TECHNICAL FIELD

The present disclosure relates generally to transportation systems and more particularly to systems and methods for coordinating various types of transportation needs in healthcare, travel, hospitality, event, dining and entertainment, and other settings.

BACKGROUND

Transportation is often cited as a barrier to healthcare access. Some sources report that 25% of low income patients miss appointment due to transportation problems. In one analysis, 82% of families who kept appointments had access to a car, while only 58% of families who missed appointments had access to a car. While public transportation can be helpful, bus users are twice as likely to miss healthcare appointments as car users.

The inability of a patient to show up, on time, for an appointment can have patient impacts, such as rescheduled or missed appointments, delayed care, and delayed or missed medication use. But there also can be impacts on healthcare providers, insurers and others. For example, hospitals, clinics and other healthcare providers have fixed costs related to their facilities and equipment and expenses for medical professionals and staff, and no-show appointments lead to these facilities, equipment and staff being underutilized. One study revealed 170,000 annual no-shows in one healthcare system, which resulted in at least $18 million in lost revenue.

Additionally, many low-income patients qualify for transportation cost payment or reimbursement by their insurer (e.g., Medicaid), and no-shows can lead to wasted costs by the insurer and transportation provider. Moreover, the current ways in which qualifying patients arrange for healthcare-related transportation are cumbersome and inefficient. They also can lead to fraud, with one study reporting that Medicare paid more than $50 million in potentially fraudulent claims from ambulance companies for rides for seniors in 2015. In the interests of patients, providers, insurers and others, there is a need for improved healthcare-related transportation management and coordination.

SUMMARY

Embodiments relate to systems and methods for coordinating, arranging and/or managing transportation. In one embodiment, the systems and methods are used in healthcare systems. A patient schedules an appointment with a healthcare service or provider; a transportation coordination component receives appointment scheduling information (e.g., date, time, location) from an electronic medical record (EMR) system or an electronic health record (EHR) system used by the healthcare service or provider; and the transportation coordination component automatically contacts the patient. In one embodiment, this contact can include the transportation coordination component automatically scheduling transportation for the patient with a suitable transportation service and sending relevant information to the patient. In another embodiment, this contact can first include an inquiry to determine whether the patient needs transportation to the appointment and, if the patient responds affirmatively, the transportation coordination component then schedules transportation for the patient with a suitable transportation service. Upon completion of the ride (and optionally a return ride), the transportation coordination component coordinates billing of the ride costs, such as to the patient's insurer via the EMR/EHR.

Embodiments also comprise analytics that enable the transportation coordination component to assist with scheduling appointments and rides in system-efficient and cost-effective ways. These analytics can use backend data to predict behaviors and events within the system and apply predictive analytics to improve patient outcomes and system performance.

While embodiments have many applications within healthcare systems, other applications exist, including in the travel, hospitality and other industries.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures.

FIG. 4J is a partial chatbot flow diagram according to an embodiment.

FIG. 8A is a screen-capture of a user interface of a healthcare transportation coordination system to a patient according to an embodiment.

FIG. 8B is a screen-capture of a user interface of a healthcare transportation coordination system to a patient according to an embodiment.

FIG. 8C is a screen-capture of a user interface of a healthcare transportation coordination system to a patient according to an embodiment.

FIG. 8D is a screen-capture of a user interface of a healthcare transportation coordination system to a patient according to an embodiment.

FIG. 8E is a screen-capture of a user interface of a healthcare transportation coordination system to a patient according to an embodiment.

FIG. 8F is a screen-capture of a user interface of a healthcare transportation coordination system to a patient according to an embodiment.

FIG. 9A is a screen-capture of a user interface of a healthcare transportation coordination system to a patient according to an embodiment.

FIG. 9B is a screen-capture of a user interface of a healthcare transportation coordination system to a patient according to an embodiment.

FIG. 9C is a screen-capture of a user interface of a healthcare transportation coordination system to a patient according to an embodiment.

FIG. 9E is a screen-capture of a user interface of a healthcare transportation coordination system to a patient according to an embodiment.

FIG. 9F is a screen-capture of a user interface of a healthcare transportation coordination system to a patient according to an embodiment.

FIG. 9G is a screen-capture of a user interface of a healthcare transportation coordination system to a patient according to an embodiment.

Figure 1:
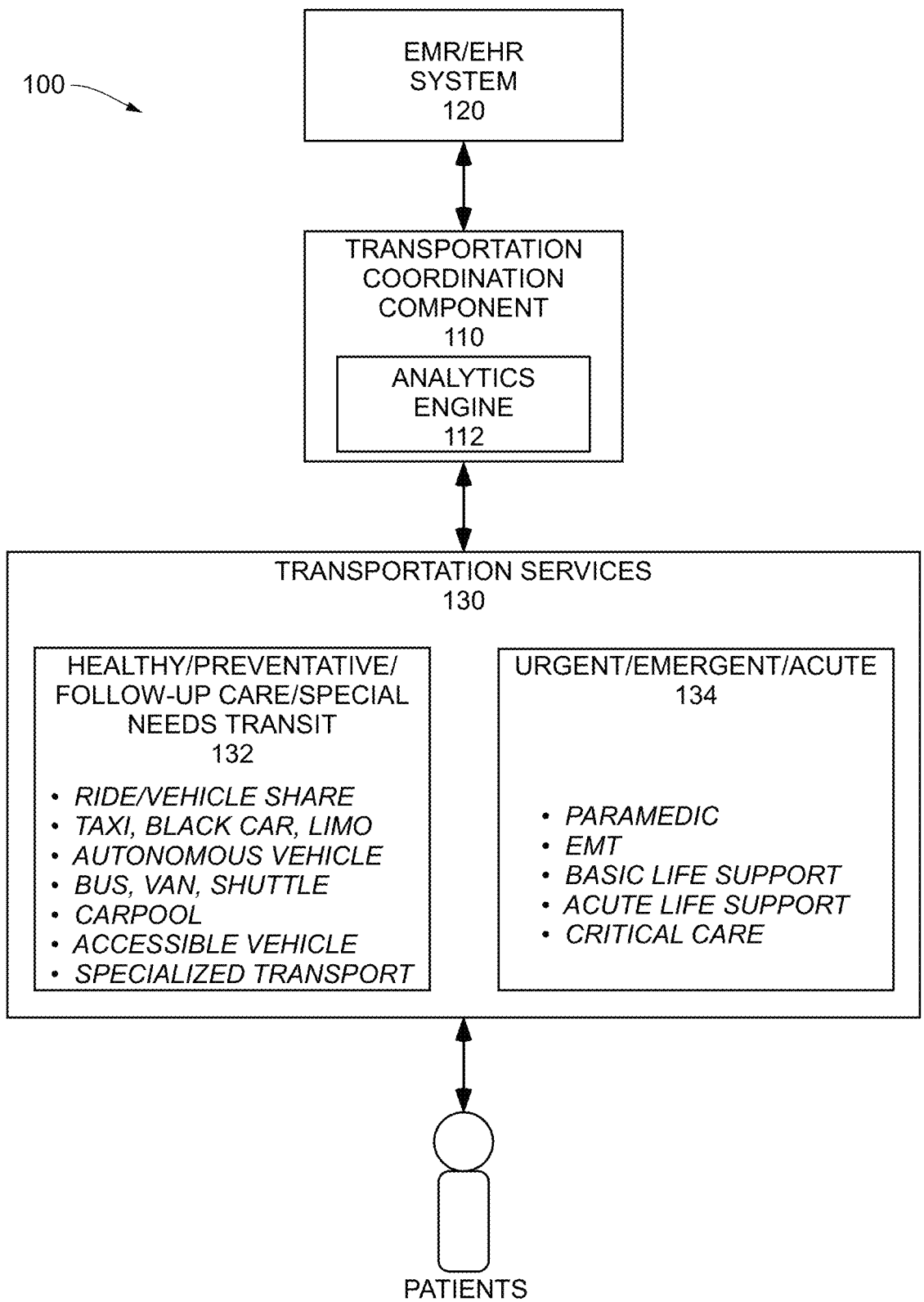
FIG. 1 is a block diagram of a healthcare transportation coordination system according to an embodiment.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

Embodiments relate to systems and methods for coordinating, arranging and/or managing transportation. These systems and methods can be used and applied in a variety of settings and industries, including healthcare, travel, hospitality, event, dining and entertainment, and others. Though examples used herein primarily relate to healthcare settings, embodiments are not limited thereto.

In one example embodiment, a patient schedules an appointment with a healthcare service or provider; a transportation coordination component receives appointment scheduling information (e.g., date, time, location) from an electronic medical record (EMR) system or an electronic health record (EHR) system used by the healthcare service or provider; and the transportation coordination component automatically schedules suitable transportation for the patient. In a variation of this embodiment, the transportation coordination component first contacts the patient to determine whether the patient needs transportation to the appointment and, if so, the transportation coordination component then schedules transportation for the patient with a suitable transportation service. The type, suitability or other information related to the patient and his or transportation needs can be determined by a filter applied by the transportation coordination component to available data and information, including from the patient's EMR/HER. Upon completion of the ride (and optionally a return ride), the transportation coordination component coordinates billing of the ride costs, such as to the patient's insurer via the EMR/EHR.

Referring to FIG. 1, an embodiment of a healthcare transportation coordination system 100 is depicted. System 100 comprises a transportation coordination component 110 that is communicatively coupled with at least one EMR/EHR system 120 and at least one transportation service 130.

Transportation coordination component 110 can comprise a combination of hardware and software that enables component 110 to communicatively couple with EMR/EHR system 120 and transportation service 130. In one embodiment, transportation coordination component 110 can be so-called "middleware," software that resides on one or more computing devices (e.g., at least one server in communication with at least one processor and a memory) and provides services to software programs and applications beyond those available from the operating system. In some embodiments, transportation coordination component 110 can comprise plug-in or tool bar features that can be integrated with or embedded in other programs (from the perspective of a user of another program), such as EMR/EHR system 120. In these embodiments, transportation coordination component 110 can operate seamlessly with EMR/EHR system 120 from a user's perspective, thereby providing additional features and functions not otherwise available in EMR/EHR system 120. In other embodiments, transportation coordination component 110 can comprise a separate or stand-alone application ("app," with an application program interface, API), program, window or other arrangement that, while communicatively coupled with other programs such as EMR/EHR system 120 in the background, appears to be distinct from a user's perspective. In yet another embodiment, there is no ongoing communicative coupling between EMR/EHR system 120 and transportation coordination component 110. Instead, information is exchanged periodically or on-demand. For example, information regarding all of the appointments scheduled and related patient data can be sent by EMR/EHR system 120 to transportation coordination component 110, such as in a .CSV file, daily, weekly or in some other time interval. Such an embodiment can be useful initially as experience and comfort levels with transportation coordination component 110 increase, leading to eventual direct integration between EMR/EHR system 120 and transportation coordination component 110.

In any configuration, the hardware supporting the software components of transportation coordination component 110 can comprise servers, computers, routers and other devices. In still other embodiments, an additional middleware component or service, such as one provided by Sansoro Health, Redox or another provider, can interface with, provide access to and/or exchange information with EMR/EHR 120 for transportation coordination component 110.

In embodiments, transportation coordination component 110 comprises an analytics engine 112. Analytics engine 112 can apply various filters and perform various analyses of criteria and characteristics related to one or more of a patient, a healthcare provider, a transportation service, an appointment, real-time traffic and weather conditions, and other factors to provide feedback and suggestions for appropriate scheduling, transportation, and other tasks within system 100. For example, analytics engine 112 can apply various filters to information available in or from EMR/HER 120 for a particular patient to determine, for example, patient demographics, care needs, language abilities, relative locations, and other information useful in scheduling appointments and arranging related transportation. The filters can use publicly available information as well, such as weather reports and real-time traffic updates. In some embodiments, analytics engine 112 can utilize machine learning, data mining, predictive analytics, and other techniques to improve any of its selection, use or application of data. Analytics engine 112 and its uses are discussed in more detail below.

In some embodiments, transportation coordination component 110 is communicatively coupled with EMR/EHR system 120 via a local and/or wide-area network, such as the internet, an intranet, an internal network (such as within a hospital or healthcare facility), a wireless network, a cellular network, a satellite network and/or other networks. Those skilled in the art will appreciate that communicative couplings between components and systems can be implemented in a variety of ways using a variety of means and modes, and particular implementations can vary depending on a variety of factors, including network availability, network capacity, security requirements, and others. In one example embodiment, the internet and a local hospital or other healthcare system network form the primary communicative coupling between transportation coordination component 110 and EMR/EHR system 120.

Generally speaking, an EMR or EHR comprises a digital version of a patient's health records and medical history. A particular patient may have several EMRs/EHRs, such as one at or associated with each healthcare provider. Some healthcare providers coordinate access to EMRs and EHRs while others maintain their own EMRs and EHRs, though in some contexts EMRs may be considered to be specific to a healthcare provider while EHRs may follow a patient from provider to provider. EMR/EHR system 120 is a system that manages and implements EMRs and EHRs. Example EMR/EHR system providers include EPIC, Cerner, Allscripts, Athena Health, Optum, Kareo and many others. The particular EMR/EHR system 120 used in any implementation of system 100 generally is not important, as transportation coordination component 110 (or additional middleware, such as Sansoro) can be configured in embodiments to interface with any EMR/EHR system 120. Examples given herein for illustration purposes may use EPIC as an example EMR/EHR system 120, but these examples are not limiting, and an advantage of system 100 and transportation coordination component 110 is that they can be compatible with any EMR/EHR system 120.

EMR/EHR system 120 and healthcare provider practices related to handling and managing patient information must be compliant with the Health Insurance Portability and Accountability Act (HIPPA) and in embodiments can assist healthcare providers and systems with maintaining compliance with HIPPA. This can include prompting for and receiving suitable authorizations from patients to share and exchange information related to their care with insurers and others. In embodiments, this authorization can include authorizing the healthcare provider, such as via EMR/EHR system 120, to share suitable and sufficient information with transportation coordination component 110 to enable transportation coordination component 110 to communicate with the patient and transportation service 130 and arrange for transportation of the patient to healthcare appointments.

As part of a patient's health records and medical history, EMR/EHR system 120 includes patient healthcare appointment information, and in embodiments EMR/EHR system 120 is used by a provider to schedule patient appointments. Thus, in embodiments EMR/EHR system 120 can comprise or interface with a calendaring and scheduling system. These systems—or these components of EMR/EHR system 120—can be highly developed and very sophisticated with respect to identifying necessary providers (e.g., doctors, technicians, nurses), scheduling appropriate time for visits and procedures with these providers, and otherwise managing healthcare resources. In embodiments, transportation coordination component 110 utilizes this scheduling information for particular patients to arrange for related transportation, as is discussed in more detail below.

As another part of a patient's health records and medical care, EMR/EHR 120 optionally can interface with a healthcare provider billing system in some embodiments. This can comprise, in one example, interfacing with health insurer portals and systems in order to check patient insurance coverage and allowances and provide billing and reimbursement information so that the healthcare provider associated with EMR/EHR system 120 is reimbursed for services provided to the patient. Some patients (e.g., those using Medicaid) may qualify for transportation costs to be covered or reimbursed by the insurer, and in embodiments these costs also can be included in the billing and reimbursement information provided by EMR/EHR system 120 to the insurer. To facilitate this, transportation coordination component 110 can provide necessary transportation service information, such as time, date, patient, and cost, for eligible patients to EMR/EHR 120 after the transportation is completed and verified, which can simplify the process of reimbursement for these expenses. In other embodiments, reimbursements can be handled in other ways, such as directly between the insurer and transportation coordination component 110, or directly between the insurer and transportation service 130, or in some other way.

Patients can have a variety of healthcare-related transportation needs. Oftentimes patients need transportation for non-emergency medical appointments, such as for preventative care, follow-up care, screening, lab, and other issues for which appointments can be scheduled in advance by days, weeks or even months. Sometimes patients need specialty transportation, such as wheelchair-accessible transportation, bed or gurney transportation, other non-ambulative transportation, transportation that can provide basic life support, and other types of transportation requiring specialized or suitable vehicles and/or transportation staff. Still other patients may require transportation capable of providing acute life support, which may be needed in emergency or non-emergency situations.

Thus, transportation service 130 can comprise at least one or a plurality of different transportation providers and options in one embodiment, generally falling into one of two categories: healthy/preventative/follow-up care/special needs transportation services 132, and urgent/emergent/acute transportation services 134. In various embodiments, transportation services 132 can comprise any of a taxi service, a van or bus service, a ride-sharing service (e.g., UBER, LYFT), a vehicle-sharing service (e.g., CAR2GO), an autonomous or self-driving vehicle service, a carpool, a service that provides accessible and/or specialized transportation (e.g., wheelchair accessible, gurney accessible), a black car or other limo service, a public transportation service, or some other type of transit or transportation service. Transportation services 134 can include any of an ambulance, paramedic service, emergency medical technician (EMT) service, basic life support service, acute life support service (e.g., helicopter), critical care service, or some other type of transit or transportation service. These categories are not necessarily exclusive, and there can be overlap and cross-over between them; for example, in some urgent (but not emergent) situations, a taxi or rideshare service may be a suitable transportation service, or a van service may include basic life support services. Regardless of the transportation service used or its format, transportation coordination component 110 is configured to be communicatively coupled with transportation service 130 to coordinate transportation for patients or others needing transportation.

The communicative coupling between transportation coordination component 110 and transportation service 130 can comprise a variety of different communication methods and modes. In one embodiment, and similar to some embodiments of the communicative coupling between transportation coordination component 110 and EMR/EHR system 120, the communicative coupling can comprise the internet, such as a web interface. This type of coupling can be used, for example, for communications between transportation coordination component 110 and transportation service 130 comprising a ride-sharing service that utilizes an API or web interface to communicate with both its riders and its drivers. In some embodiments, portions of transportation service 130's API or other interface can be presented by transportation coordination component 110 in one or more of its interfaces, providing a seamless and integrated appearance to users at, e.g., healthcare provider 122. In another embodiment, the communicative coupling can comprise a telephone or cellular connection, such as with a taxi dispatch service. In yet another embodiment, the communicative coupling can comprise an emergency services interface (e.g., via the internet, another network connection, or a phone or cellular connection) to receive communications from a 911 or other emergency call service, which may receive medical transit-related calls that are not emergent and therefore can be transferred to system 100 instead. The particular communications sent and received via the communicative coupling can be accomplished via email, text message (e.g. SMS, iMessage, or similar services), video conferencing (e.g., Facetime, Skype), digital communications between web interfaces (e.g., API-to-API communications), phone calls (landline or cellular), and others, using virtually any wired or wireless (e.g., wifi, Bluetooth, near-field communication or NFC, cellular) communication format.

In some embodiments, text messaging is the primary mode of communication, particularly with patients, as it is broadly available, relatively inexpensive, fast, and reliable. Moreover, it is often a familiar and preferred mode of communication for patients. If patients are visually impaired or prefer voice communications, automated voice calls implemented by a "chatbot" (discussed below) can be used instead.

Figure 2:
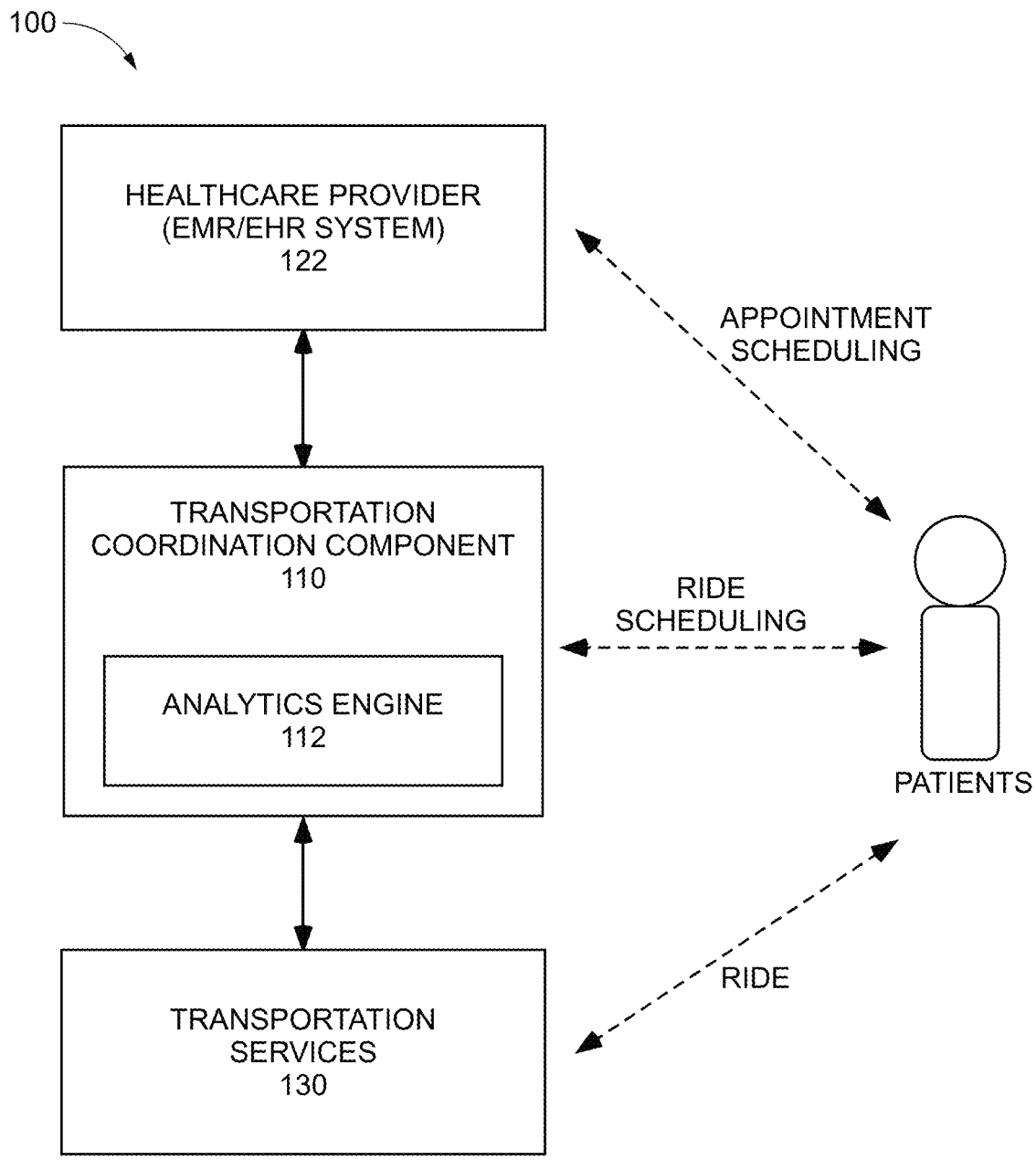
FIG. 2 is another block diagram of a healthcare transportation coordination system according to an embodiment.

Referring also to FIG. 2, which is another depiction of system 100 of FIG. 1, in embodiments there are also communicative couplings between the patient and each of transportation coordination component 110, a healthcare provider 122 (e.g., the home or user of EMR/EHR system 120), and transportation service 130. For example, the patient will communicate with healthcare provider 122 to schedule an appointment. This can be done in person, by phone (landline or cellular), via an online scheduling portal or app of healthcare provider 122 (e.g., via the internet), by email, by text message, or in some other way. Scheduling an appointment can trigger transportation coordination component 110 automatically contacting the patient to arrange or confirm transportation. In some embodiments, transportation coordination component 110 can first inquire whether the patient wants or needs transportation, though this is optional. The patient can communicate via or directly with transportation coordination component 110 to confirm transportation needs, schedule transportation, receive reminders, and/or exchange other communications related to arranging and receiving transportation. Finally, the patient will also communicate with transportation service 130, such as with a driver in person when receiving transportation, or via text, email, app-to-app, or other communications, and/or in other ways.

In other embodiments, these communicative couplings with the patient can be coordinated or facilitated by a single entity (at least with respect to the patient's perception), such as transportation coordination component 110 or even healthcare provider 122 in some embodiments. In still other embodiments, some activities can be coordinated automatically. These arrangements can reduce the communications burden on the patient and provide increased convenience and efficiency overall.

Figure 3:
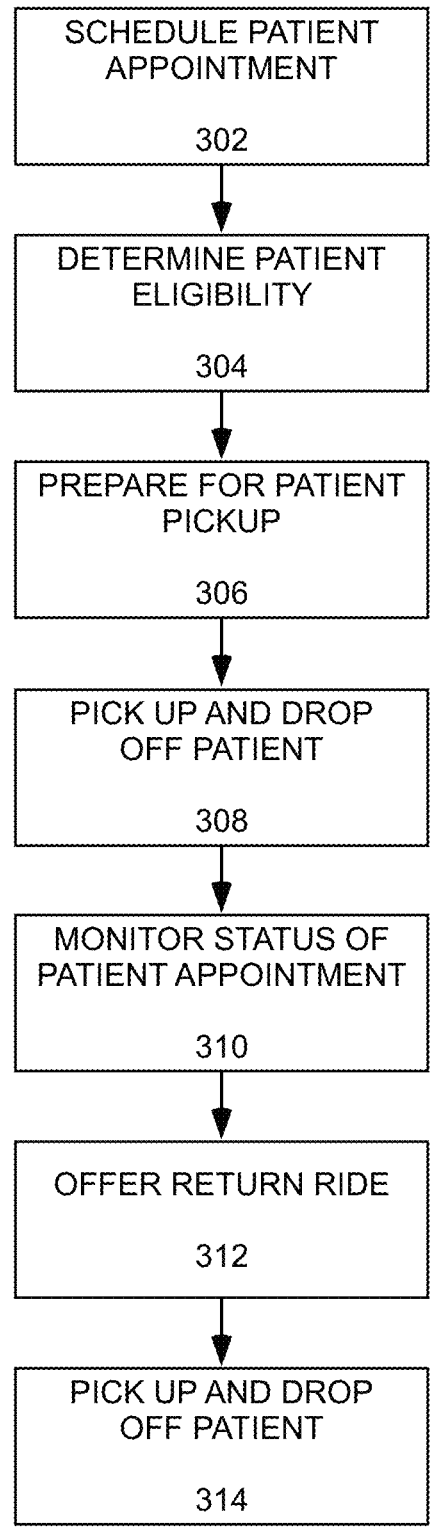
FIG. 3 is a flowchart of a method related to a healthcare transportation coordination system according to an embodiment.

An overview flow of a method related to an embodiment of system 100 is depicted in FIG. 3. At 302, a patient schedules an appointment with healthcare provider 122 that is captured in the patient's record in EMR/EHR system 120.

In some embodiments, analytics engine 112 of transportation coordination component 110 can assist with setting up appointments by determining which appointments a patient is most likely to show up for and suggesting those appointment times to a scheduler via EMR/EHR system 120. Additionally (and optionally), analytics engine 112 also can consider transportation costs associated with appointment times. For example, analytics engine 112 may determine that a particular patient should only be scheduled for appointments after noon because the patient tends to cancel or not show up for appointments scheduled in the morning. Additionally, analytics engine 112 can suggest to a scheduler via EMR/EHR system 120 that the appointment be scheduled before 4 pm because transportation costs increase after this time because of surge pricing or rush hour-related delays.

In some embodiments, analytics engine 112 can review other appointments that may be scheduled by the same patient and, independently or in concert with EMR/EHR system 120, suggest or attempt to coordinate scheduling of appointments to reduce the number of trips a patient would have to make; coordinate care among multiple medical providers, departments, professionals, or other entities; and reduce costs associated with patient travel. In addition to providing advantages to patients, analytics engine 112 also can, via EMR/EHR system 120, check for available, unfilled appointments and attempt to fill them in a way that maximizes use of provider resources while at the same time providing efficiencies for patients. In one embodiment, analytics engine 112 and transportation coordination component 110 can provide prompts to a scheduler, transportation team member, or other frontline staff using EMR/EHR system 120 or otherwise working to schedule patient appointments.

Alternatively, analytics engine 112 itself or components, features or functions thereof can be incorporated directly into EMR/EHR system 120 in some embodiments. For example, appointment scheduling-related filters and functions of analytics engine 112 can be incorporated into EMR/EHR system 120, while transportation scheduling-related filters and functions of analytics engine 112 can be incorporated into transportation coordination component 110, with the two being in communication and coordination with one another. In yet another embodiment, analytics engine 112 can be a standalone entity that interfaces and communicates with both EMR/EHR system 120 and transportation coordination component 110.

Appointment scheduling and other suggestions can be provided in EMR/EHR system 120 via the communicative coupling between transportation coordination component 110 and EMR/EHR system 120 or they can be recorded in a patient's record in EMR/EHR system 120 so that a scheduler has access to them. In yet another embodiment, the scheduling component of EMR/EHR system 120 can only make available to the scheduler appointments that are suitable for that particular patient when scheduling is being performed, reducing the information that must be manually considered by the scheduler while also using the results of analytics engine 112 and services provided by transportation coordination component 110 to assist with scheduling that will help to decrease missed appointments by analyzing specific patient performance and behaviors along with transportation data. Other uses and applications of analytics engine 112 are discussed elsewhere herein.

At 304, patient eligibility for appointment transportation is determined. In one embodiment, this determination can be made by healthcare provider 122, such as from information about the patient and/or the patient's insurance available in EMR/EHR system 120. Once this determination is made, it can be stored in the patient's record in EMR/EHR system 120 so that the eligibility determination need not be repeated in the future, though because eligibility may change over time it may need to be confirmed again later (and in some embodiments this can be done automatically by transportation coordination component 110). In another embodiment, this determination is made by transportation coordination component 110, such as upon receiving and filtering patient information from EMR/EHR system 120 and, if necessary, reviewing the criteria to determine eligibility.

In some embodiments, the order of tasks 302 and 304 can be reversed. Additionally, insurers, such as Medicaid, may require that eligibility be confirmed periodically, such that the determination shown at 304 in FIG. 3 is repeated elsewhere in the process (e.g., before 308) at each appointment or patient interaction, or according to some frequency (e.g., monthly, quarterly, annually).

In still other embodiments, all patients that schedule with a particular facility or who meet some basic criteria are automatically contacted about transportation, with pricing information also provided to those patients who personally pay for their transportation. Thus, task 304 can be omitted entirely or adapted according to meet the needs of particular users.

At 306, preparations are made for patient pick-up. EMR/EHR system 120 provides patient and appointment information (e.g., first and last name, patient ID, appointment date and time, healthcare department, pick-up address, phone number) to transportation coordination component 110, and the patient and appointment information is also stored in a database (not shown) of transportation coordination component 110. With this information, transportation coordination component 110 can then contact the patient to arrange transportation for the appointment.

Figure 4A:
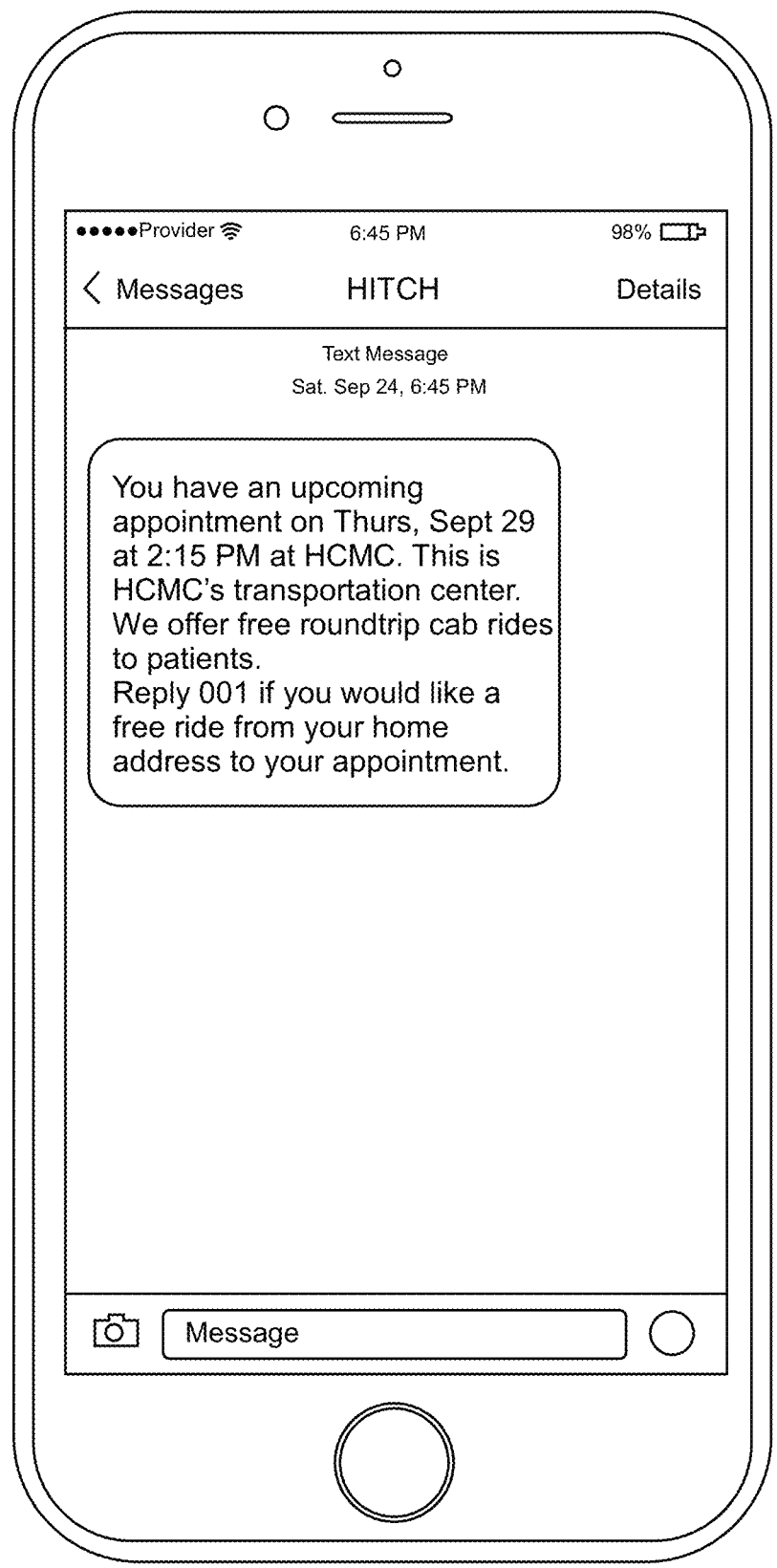
FIG. 4A is a screen-capture of a text message sent by a healthcare transportation coordination system to a patient according to an embodiment.

In one embodiment, this can be done via a text or SMS message from transportation coordination component 110 to the patient, an example of which is depicted in FIG. 4A. The SMS messages and the specific text shown in FIGS. 4A-4I are only examples, and more or fewer messages may be sent, and/or different text may be used in some circumstances or embodiments. For example, in one embodiment transportation coordination component 110 implements or interfaces with a "chatbot," a computer program that conducts conversations via auditory or text messages. Chatbots can be more intuitive than some other text or voice services. For example, while the example shown in FIG. 4A requires a patient to send a particular reply ("001"), some chatbots can recognize more intuitive replies from patients, such as "yes," "yeah," "please" and other affirmative responses, or can prompt for more information or follow-up when replies are not clear. Chatbots also can recognize and use emojis, sounds, pictures, symbols and other audible and visual communication components. Chatbot scripts also can be easily customized and updated as needed. An example of a chatbot flow diagram is shown in FIG. 4J.

Additionally, while the examples in FIGS. 4A-4J are shown in the English language, system 100 can provide the option of sending the messages in other languages in order to reach additional patient populations and communicate with patients in the language with which they are most comfortable or prefer. In embodiments in which a chatbot is used, the chatbot can detect a preferred language from a response (e.g., "si" instead of "yes" would cause the chatbot to switch from English to Spanish). Other patient preferences also can be accommodated (e.g., voice vs. text), and they can be stored in transportation coordination component 110, the patient's record in EMR/EHR system 120, and/or in a database or other data structure accessible to one or more components of system 100.

Figure 4B:
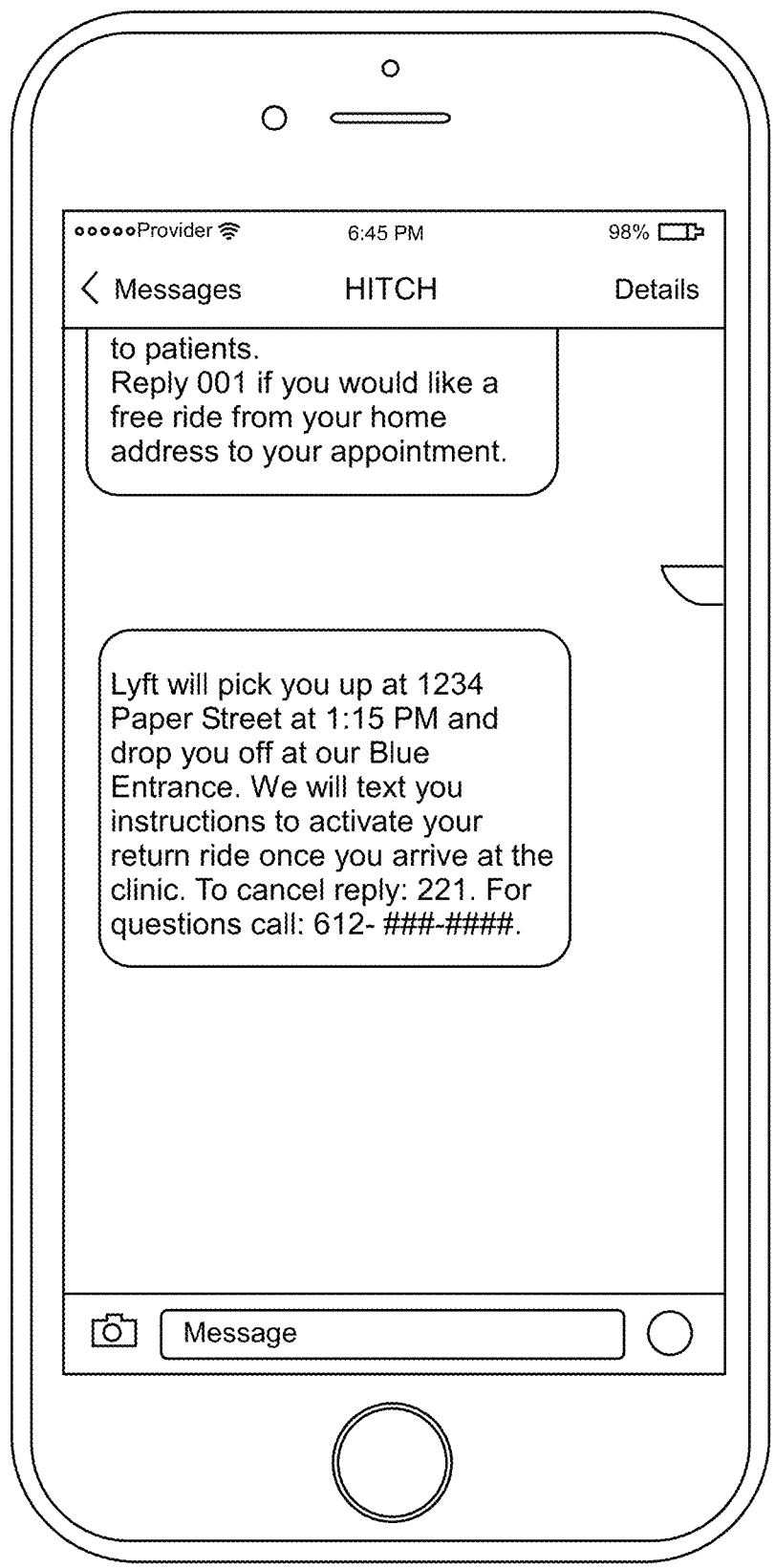
FIG. 4B is a screen-capture of a text message sent by a healthcare transportation coordination system to a patient according to an embodiment.

If the patient accepts, transportation coordination component 110 arranges for a ride and sends a ride agenda to the patient, again via text message or the patient's preferred mode of communication. An example message associated with this is depicted in FIG. 4B.

Arranging for the ride and preparing for patient pick-up can comprise a variety of different tasks, depending on the patient, type of transportation needed, types of transportation available, cost cap (if applicable) and other factors. In the example used herein, a ride-sharing service (e.g., LYFT) is used. Transportation coordination component 110 can make a determination of the appropriate transportation service 130 to use at the time of scheduling or closer in time the appointment, and adjustments can be made. For example, the ride agenda in FIG. 4B indicates that LYFT will be used, and this agenda might be texted to the patient some time in advance. If, on the day or at the time of the appointment, transportation coordination component 110 determines that LYFT is no longer available, suitable or cost-effective, transportation coordination component 110 can select a different provider from the available transportation services 130 and provide an update to the patient.

Some services (e.g., specialty medical transport, taxis, and others) may enable transportation coordination component 110 to reserve transportation resources in advance of appointments. Others, such as ride-sharing services like UBER and LYFT, may require transportation coordination component 110 to calculate a patient pick-up time and coordinate request of transportation service at an appropriate time on the day of the appointment. Thus, in embodiments transportation coordination component 110 is in real-time communication with these services 130 in order to coordinate timely and effective service for patients. This coordination can be carried out according to determinations made by analytics engine 112, which can carry out analyses of factors related to transport of a particular patient according to that patient's particular characteristics and needs in order to determine the most appropriate transportation service 130 to use for a particular appointment. This can comprise one or more of analyzing a patient pick-up location and patient drop-off location, reviewing an appointment time, estimating a travel time, estimating a pick-up lead time between requesting the ride and service 130 actually picking up the patient, estimating a patient transfer time from drop-off to appointment check-in, reviewing a patient history of timeliness and preferences, and estimating the transportation cost. In some embodiments, analytics engine 112 can request or receive of this information from transportation service 130 (e.g., ride-sharing services typically provide cost and time of travel estimates in their apps, and analytics engine 112 can retrieve this information accordingly). Costs for some transportation services 130 can vary widely, depending on the time of day (e.g., rush hour is more expensive than mid-morning), type of transportation needed, and other factors. Transportation coordination component 110, via analytics engine 112, can consider all of these things in arranging for a ride, whether that ride is arranged for in advance and pre-scheduled, or whether that ride is requested on-demand on the day of the appointment.

Figure 4C:
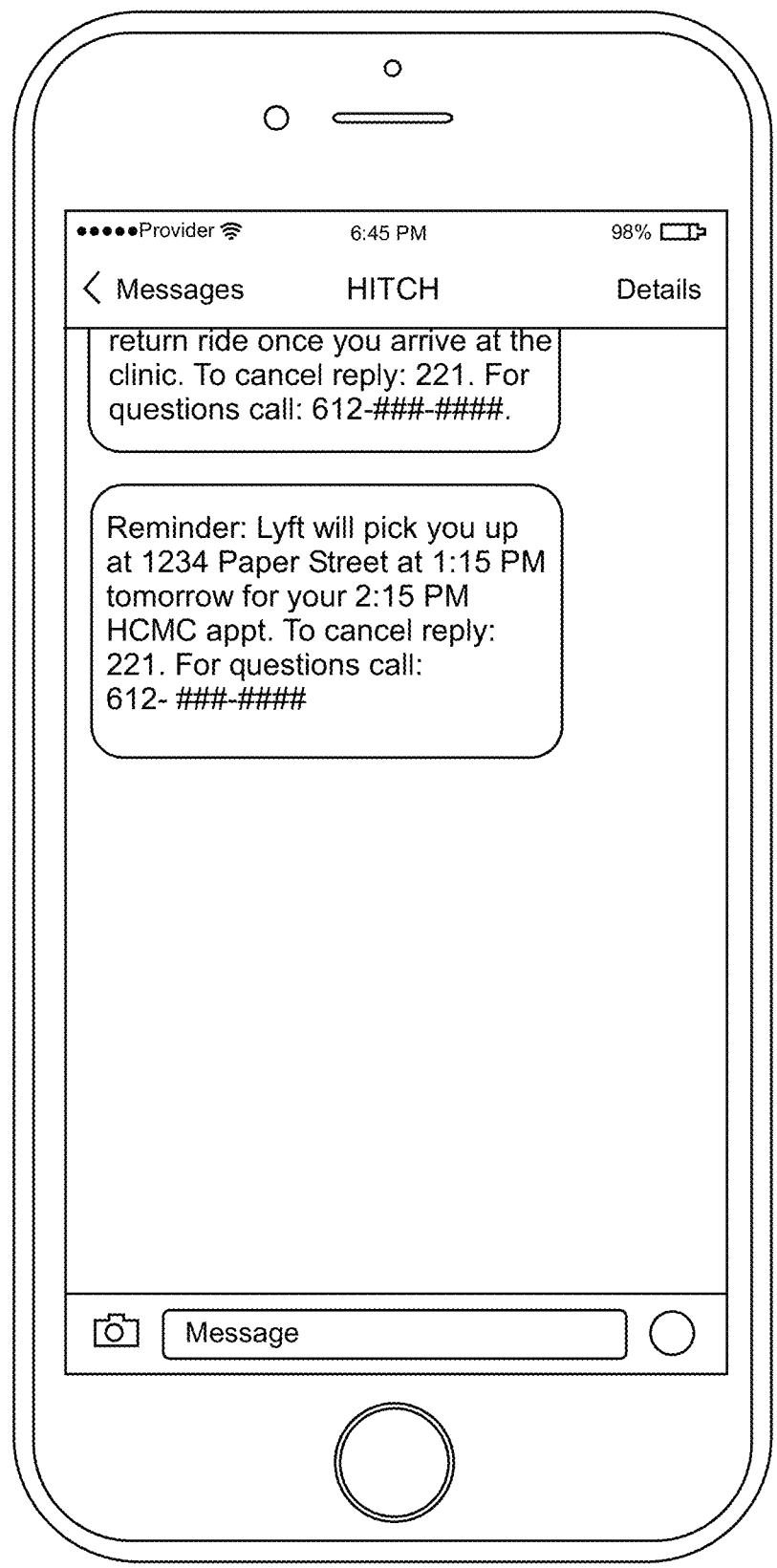
FIG. 4C is a screen-capture of a text message sent by a healthcare transportation coordination system to a patient according to an embodiment.

Once the patient has opted-in for transportation and transportation coordination component 110 has made a determination of the transportation service 130 to use and when to request that service for the patient (and still as part of task 306 in FIG. 3), transportation coordination component 110 can send reminders to the patient. These reminders can be sent at predetermined times (e.g., one week in advance, five days in advance, three days in advance, one day in advance, on the morning of the appointment, etc.) or at times determined by analytics engine 112 to be most effective, either for a particular patient, a particular healthcare provider 122, a particular type or time of appointment, or according to some other factor. In some embodiments, healthcare provider 122 can select or customize reminders and their times and intervals, while in other embodiments they can be made according to determinations made by analytics engine 112. For example, analytics engine 112 may determine that one patient is more likely to show up for appointments if reminders are sent a week in advance, three days in advance, and one day in advance, while another patient is more likely to show up if reminder are sent a week in advance and the evening before the appointment. An example reminder text message sent to a patient the day before their appointment is depicted in FIG. 4C.

At some time interval before the patient's appointment (e.g., one hour), transportation coordination component 110 confirms the patient's appointment with EMR/EHR system 120, such as by sending the patient ID to EMR/EHR system 120 and receiving a confirmation or updated patient appointment time in reply. This prevents a ride being sent if the patient has canceled or rescheduled the appointment. In some embodiments, and additionally or alternatively to a pre-appointment confirmation check, real-time or periodic (e.g., hourly, daily, weekly) updated appointment information can be sent to or requested by transportation coordination component 110 from EMR/EHR system 120.

As previously discussed, transportation coordination component 110 makes suitable arrangements for the patient's ride, according to applicable data and information. In one embodiment in which the ride-sharing service LYFT is used, this includes requesting the ride in LYFT at a suitable time. This time can vary according to ride-sharing system resources, traffic and weather conditions, and other factors, but as previously mentioned transportation coordination component 110, specifically analytics engine 112, analyze these factors to request a particular ride for a particular patient such that the patient will arrive at the appointment on time. In some embodiments, patients may prefer to initiate the ride request on the day of the appointment themselves. In this case, a text message reminder to the patient about their appointment can include a note "Reply with 101 when you are ready for your ride" or "Are you ready for your ride?" Some patients may appreciate this additional level of control, and in some embodiments analytics engine 112 can determine which patients prefer or are eligible for this feature (e.g., patients with a history of showing up for scheduled rides on time).

The ride request by transportation coordination component 110 provides necessary information to transportation service 130, which is a ride-sharing service in the example used herein. This can include an address of the patient or a latitude/longitude of the pick-up location converted by transportation coordination component 110 from the patient's address along with the patient's name, an optional photo of the patient (which is common is ride-sharing applications), the patient's phone number, and any patient notes or preferences (e.g., uses oxygen, requires wheelchair transport, use back door instead of front door, needs help transferring, ring front door bell when arriving, etc.). Transportation coordination component 110 then awaits and confirms receipt of a ride request confirmation from transportation service 130 (e.g., LYFT).

Figure 4D:
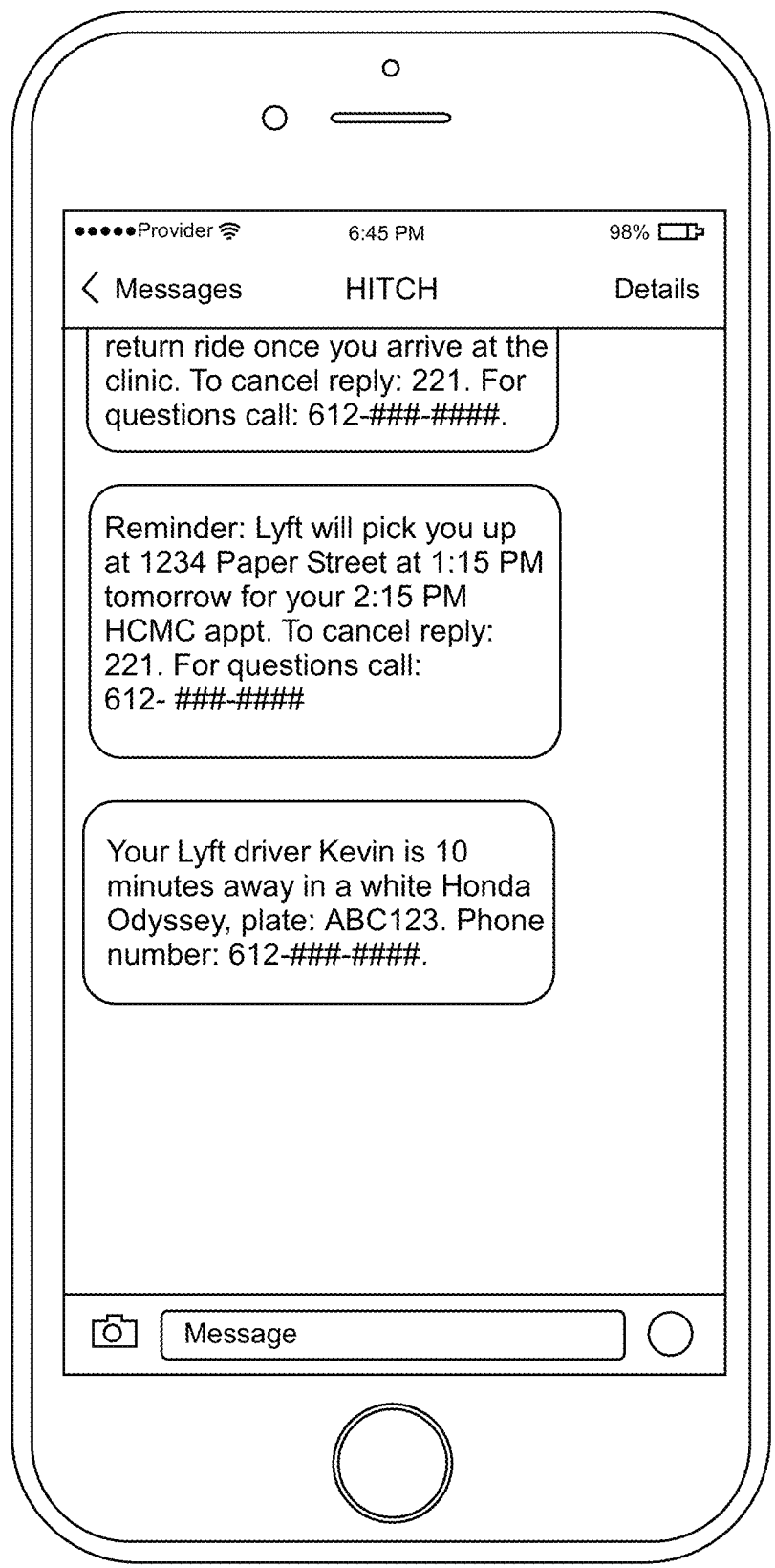
FIG. 4D is a screen-capture of a text message sent by a healthcare transportation coordination system to a patient according to an embodiment.
Figure 4E:
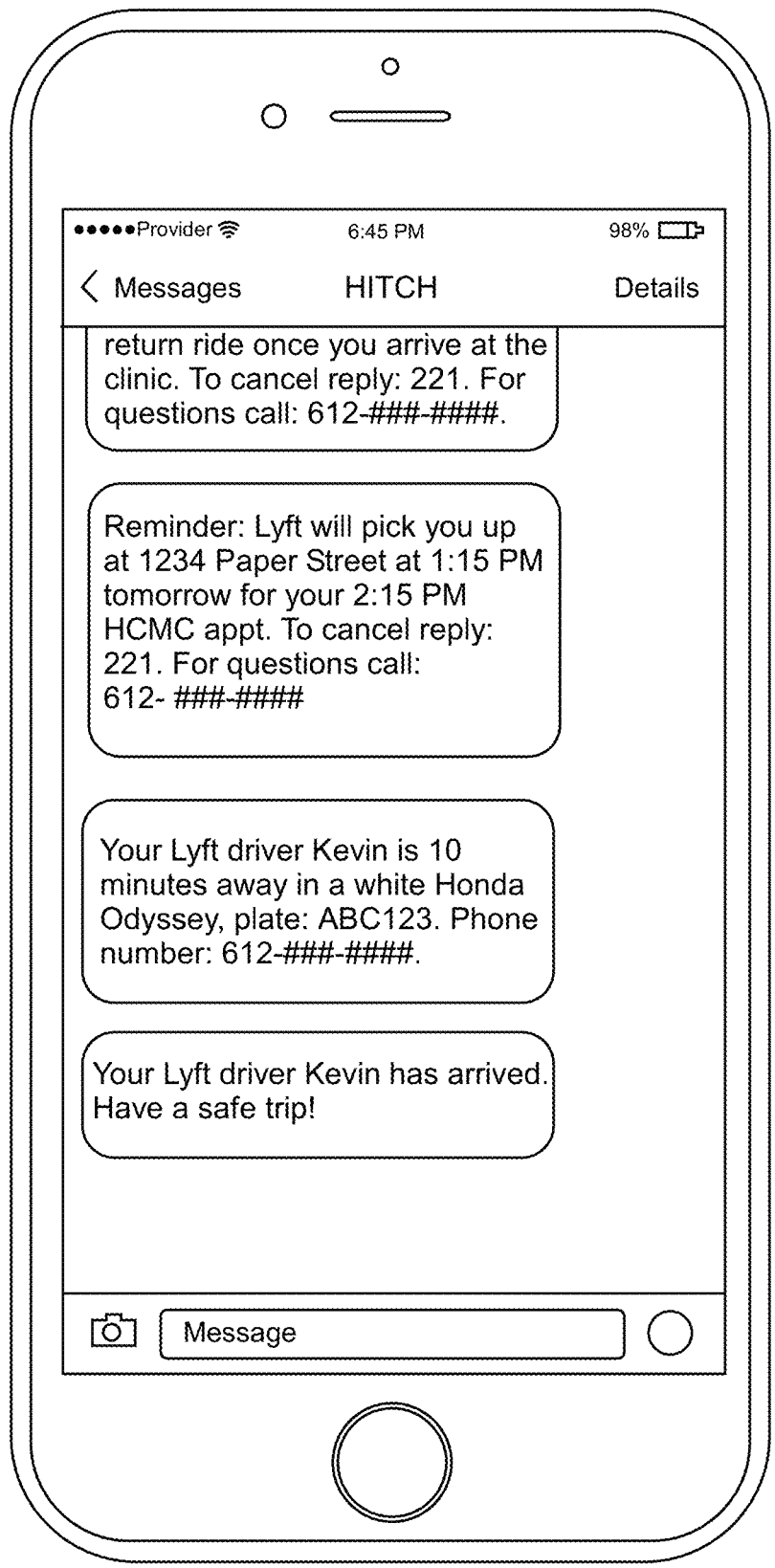
FIG. 4E is a screen-capture of a text message sent by a healthcare transportation coordination system to a patient according to an embodiment.

Once the ride is requested and on its way, transportation coordination component 110 communicates with transportation service 130 for status information (e.g., every minute or according to some other time interval) and with the patient to keep them apprised of the status and ensure the patient is ready when the ride arrives. An example status text message sent from transportation coordination component 110 to a patient is depicted in FIG. 4D, and example arrival text message sent from transportation coordination component 110 to a patient is depicted in FIG. 4E.

Those experienced with using ride sharing services will recognize that many of these types of status text messages typically are sent to users (riders) by the ride sharing service. In embodiments of system 100, however, there is no direct communication between patients (riders) and the ride sharing services. This is in part because many patients may not have the necessary ride sharing apps, may not have or wish to use personal credit cards required by the ride sharing apps, and/or may not have smartphones or data plans suitable for using ride sharing apps. In embodiments of system 100 and related methods, however, patients do not need to have or use apps because transportation coordination component 110 manages all aspects of the patient's transportation to medical appointments, including communication with and billing for the transportation services, and communication with patients. Though many patients may not have smartphones or the necessary ride sharing apps, they do not need them because system 100 utilizes basic SMS/text messages to communicate with patients. In situations in which patients cannot receive text messages, system 100, in particular transportation coordination component 110 can arrange for other types of communications, such as phone calls. This coordination and customization of communications by transportation coordination component 110 is a significant advantage of embodiments discussed herein. As previously mentioned, this coordination also can include presenting information typically present in the API of a transportation service 130 in an API or other presentation of information of transportation coordination component 110, with this information typically presented to healthcare provider 122 rather than the patient.

Figure 4F:
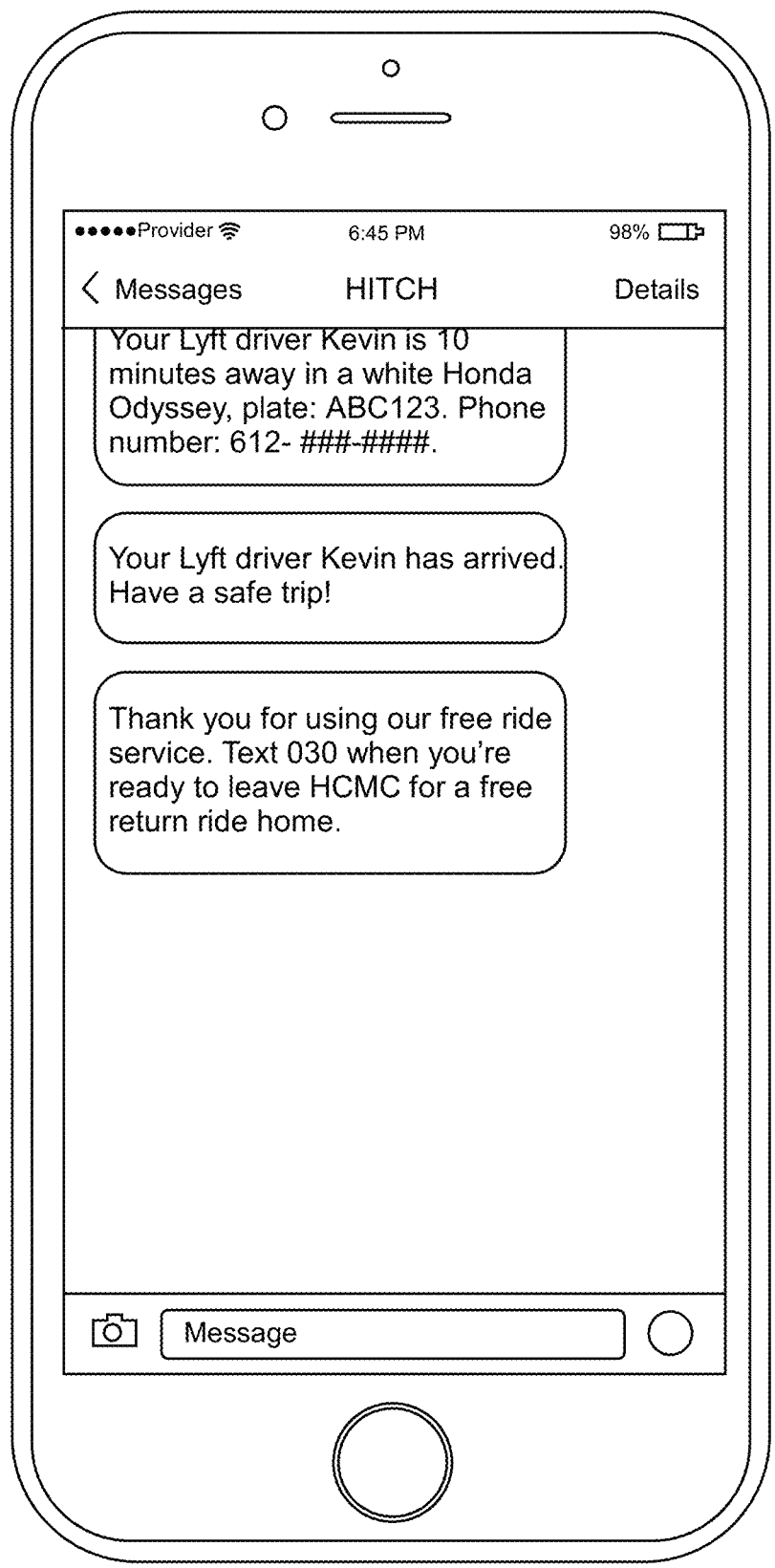
FIG. 4F is a screen-capture of a text message sent by a healthcare transportation coordination system to a patient according to an embodiment.
Figure 4G:
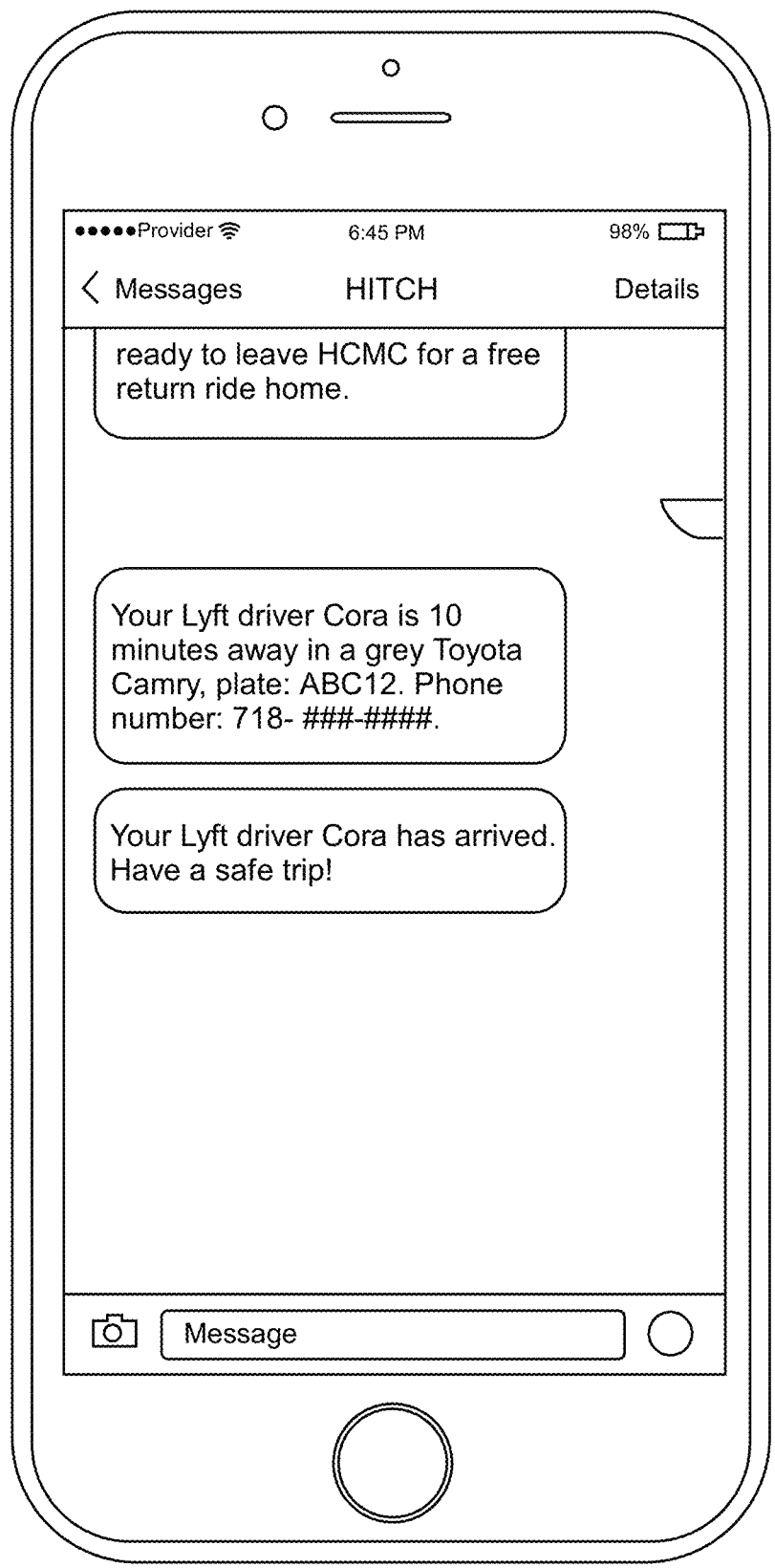
FIG. 4G is a screen-capture of a text message sent by a healthcare transportation coordination system to a patient according to an embodiment.

Returning to FIG. 3, the patient is picked up and subsequently dropped off at the appointment location at 308. Once the patient is picked up—and in fact in some embodiments before, as early as when the ride is requested by transportation coordination component 110—status information is provided in real time or periodically by transportation coordination component 110 (which is in communication with transportation service 130) to EMR/EHR system 120. This gives healthcare provider 122 estimated arrival times and updates on no-shows (e.g., transportation service 130 arrived but no patient showed up for the ride). Examples of user interfaces available to frontline staff of healthcare provider are discussed below with reference to FIGS. 7A-7F and 8A-F. At some time interval after the patient is dropped for their appointment, transportation coordination component 110 sends a text message to the patient to ask whether the patient would like return ride home. An example of this is depicted in FIG. 4F. If the patient responds affirmatively, a similar process of ride coordination and patient communications as discussed above with reference to patient pick-up is followed for arranging the ride and communicating with and picking up the patient for the return trip. Refer, for example, to FIG. 4G, which shows text messages sent to the patient to arrange for return-trip pick-up.

One difference in the return trip from the in-bound appointment trip can be status checks and communications between transportation coordination component 110 and EMR/EHR system 120 to track patient progress in their appointment (and take into account any extra time that may be necessary, such as an unscheduled lab appointment after the scheduled appointment) so that transportation coordination component 110 can request the return ride at an appropriate time and give transportation service 130 an accurate pick-up address (or latitude/longitude) and instructions. For example, the patient may need to stop at a pharmacy on the return trip in order to pick up a prescription, and transportation coordination component 110 can arrange for this by providing the address of the patient's preferred pharmacy (e.g., obtained from or via EMR/EHR system 120 or already in the database of transportation coordination component 110 if that information was previously provided) or a convenient pharmacy (e.g., one at which the patient's insurance is accepted) to transportation service 130 so that the return trip driver has all of the necessary information.

Figure 4H:
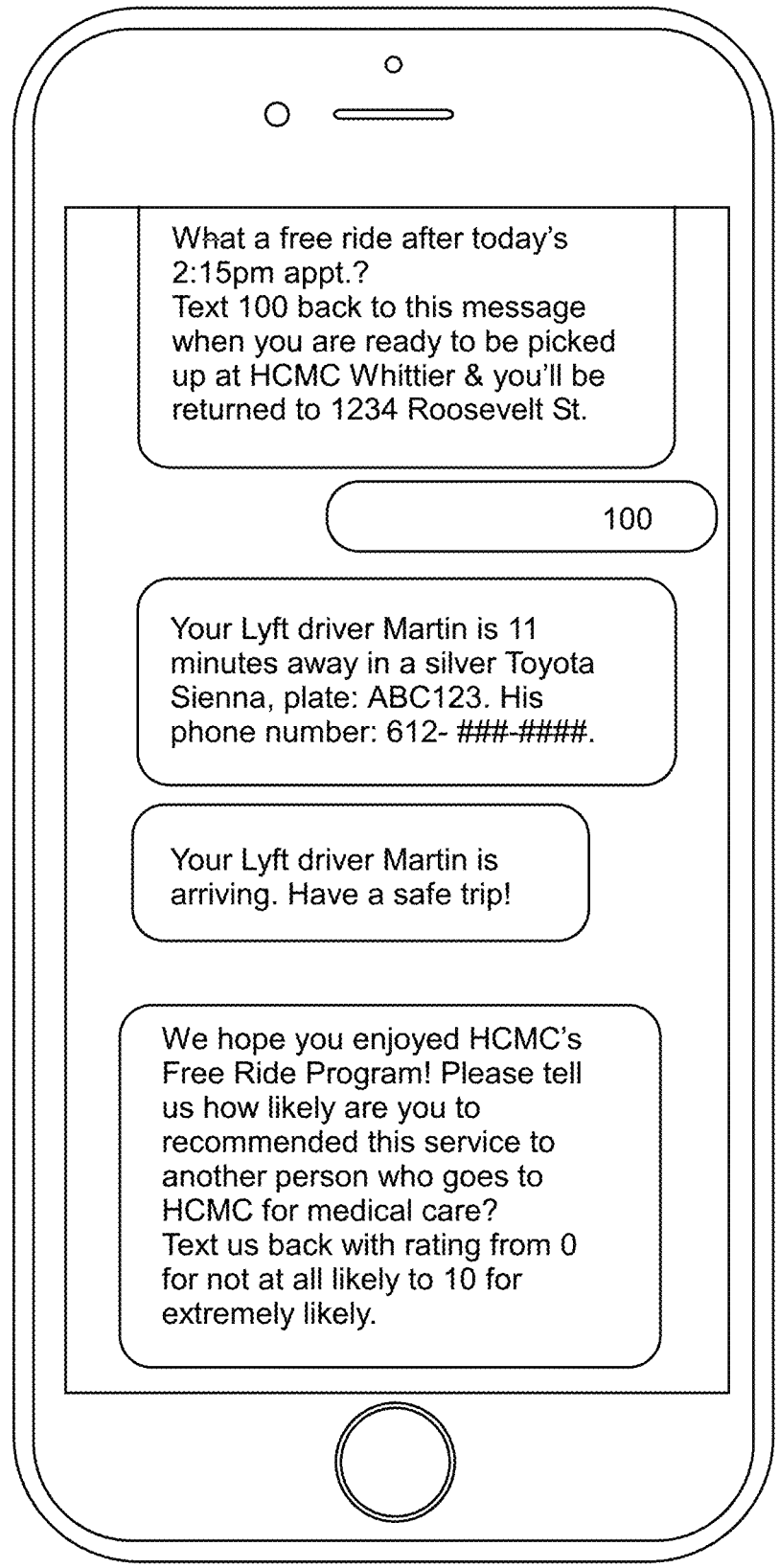
FIG. 4H is a screen-capture of a text message sent by a healthcare transportation coordination system to a patient according to an embodiment.
Figure 4I:
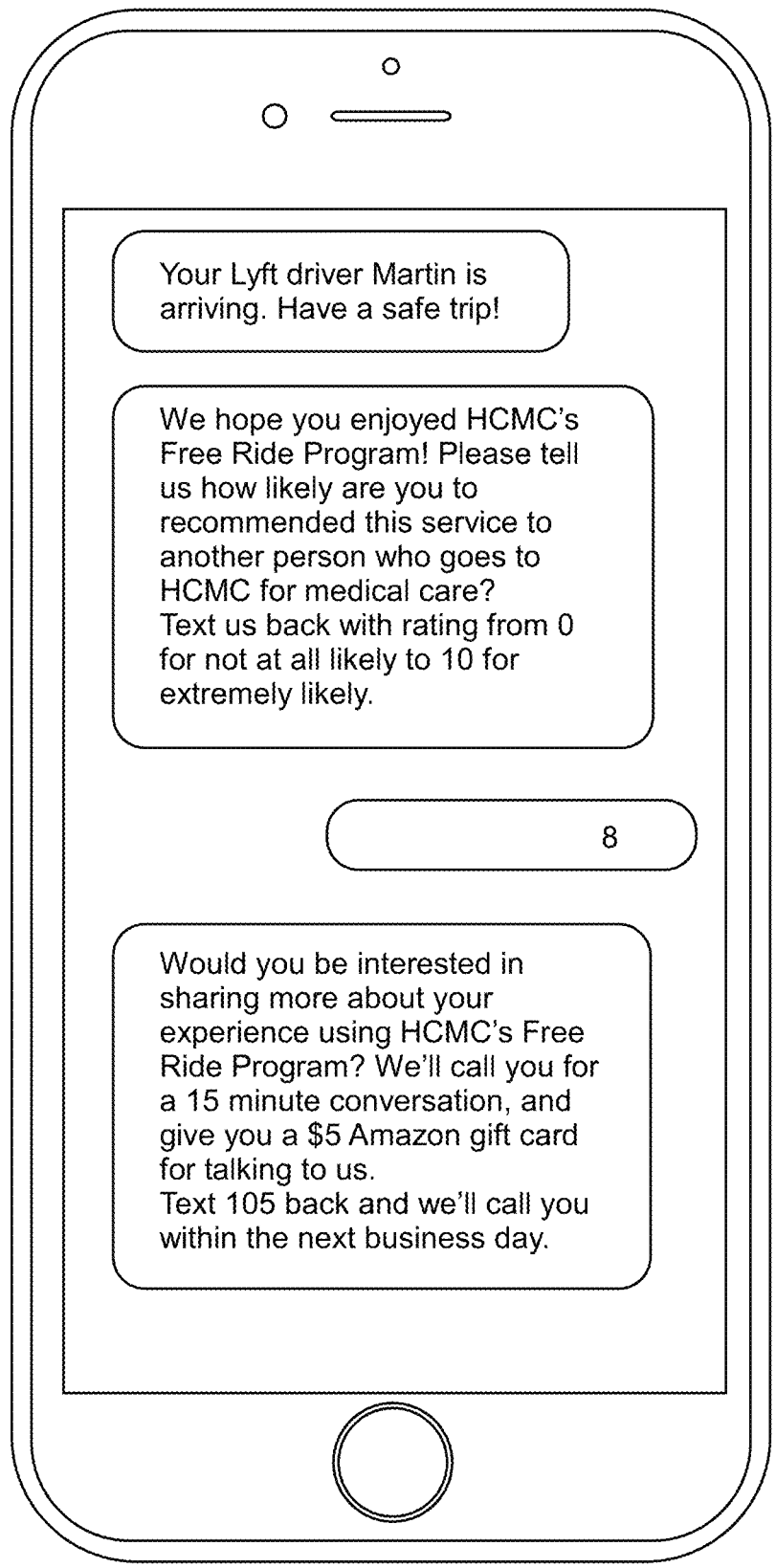
FIG. 4I is a screen-capture of a text message sent by a healthcare transportation coordination system to a patient according to an embodiment.

Transportation coordination component 110 monitors the return trip (e.g., by querying transportation service 130 every minute or in some other interval) to ensure it is completed. In some embodiments, and either with respect to the inbound (to the healthcare facility) or outbound (the return trip from the healthcare facility) trip or both, transportation coordination component 110 also can interface with EMR/EHR system 120 to confirm that the patient has an appointment, and that the patient actually checked in for and attended their appointment. This monitoring and validating of all trips coordinated by system 100 can help to reduce fraud, ensuring that the patient's insurer is only billed, and transportation service 130 is only compensated, for qualifying and actually completed rides. In some embodiments, the patient may receive a final text message some time after the return trip is completed, asking for feedback or other information in order to ensure patient satisfaction with transportation service 130 and system 100 overall. An example is depicted in FIG. 4H.

FIGS. 5A-5F are a series of flowcharts that illustrate specific tasks related to the method of FIG. 3 just discussed above. The tasks carried out are depicted from the perspective of transportation coordination component 110, in that they generally are carried out or coordinated by transportation coordination component 120.

Figure 5A:
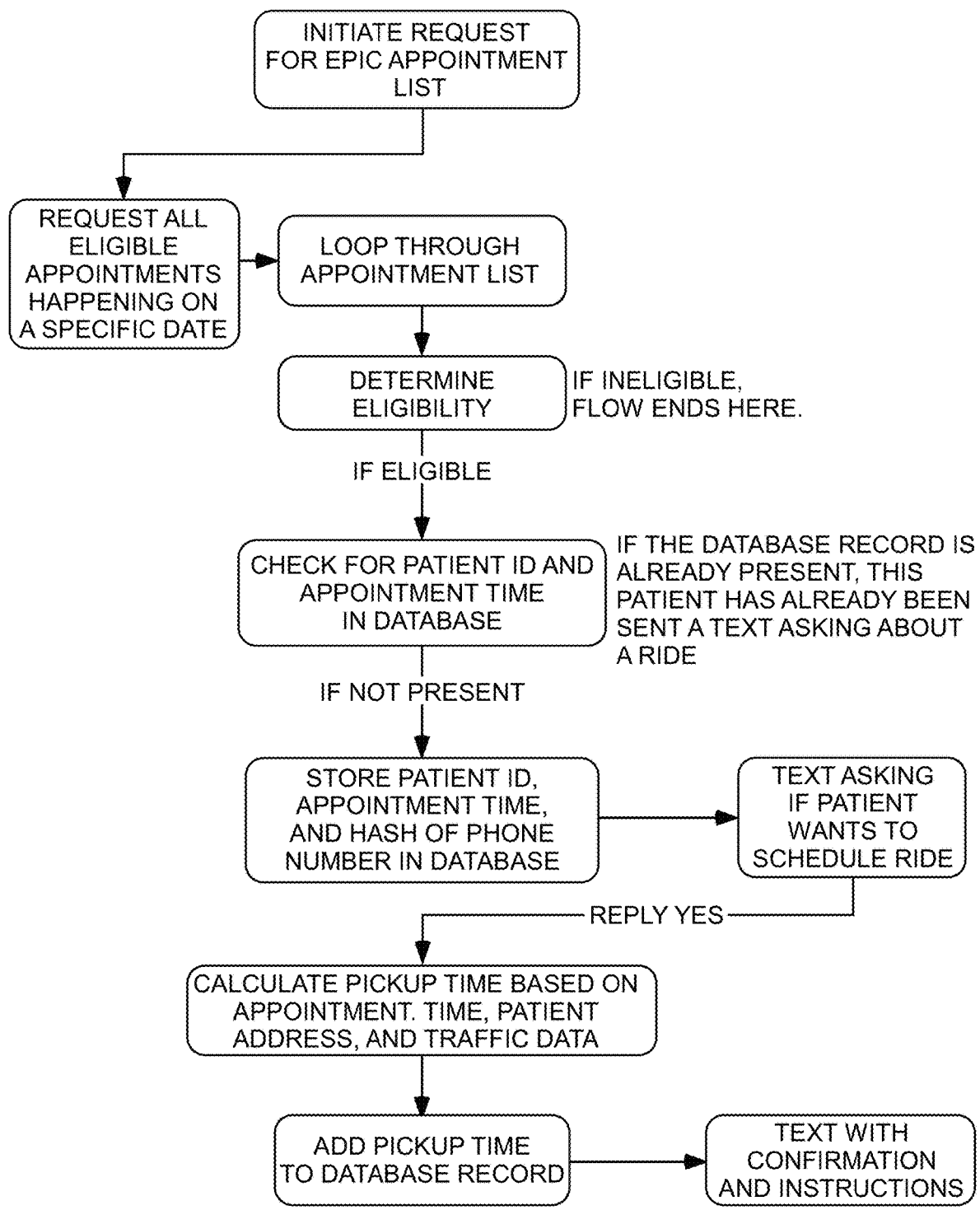
FIG. 5A is a flowchart of part of a ride coordination process according to an embodiment.
Figure 5B:
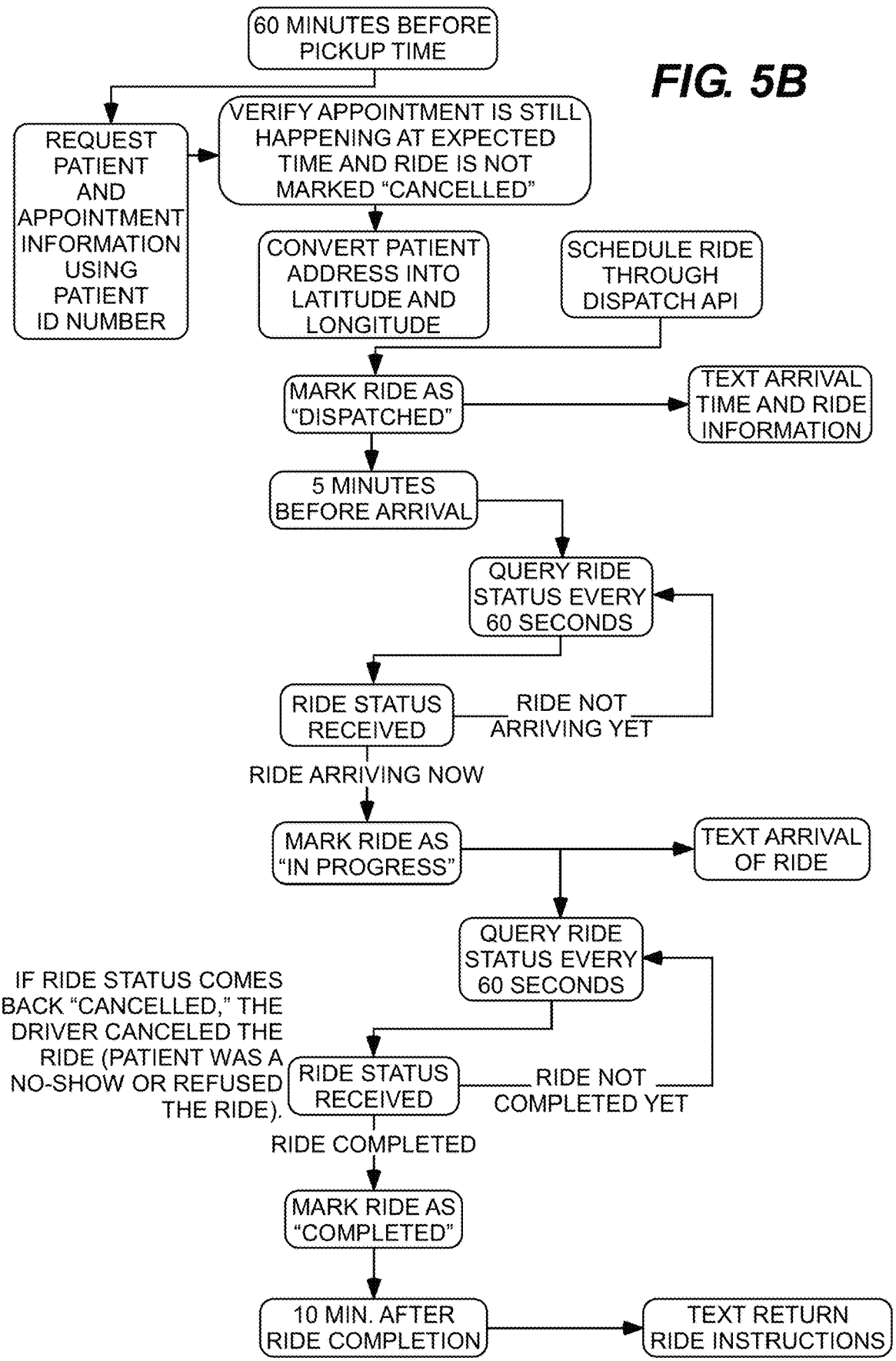
FIG. 5B is a flowchart of part of a ride coordination process according to an embodiment.
Figure 5C:
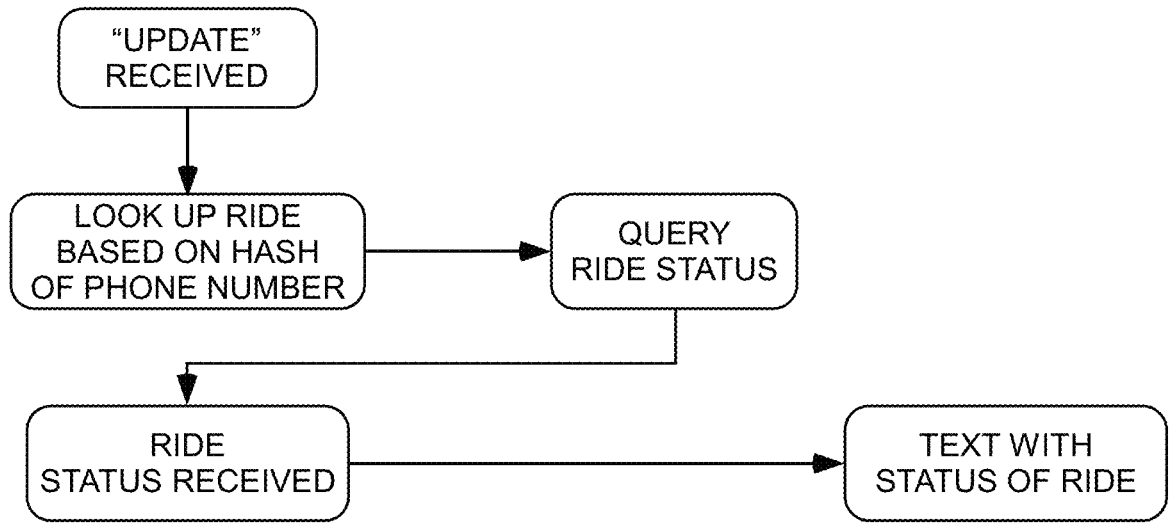
FIG. 5C is a flowchart of part of a ride coordination process according to an embodiment.
Figure 5D:
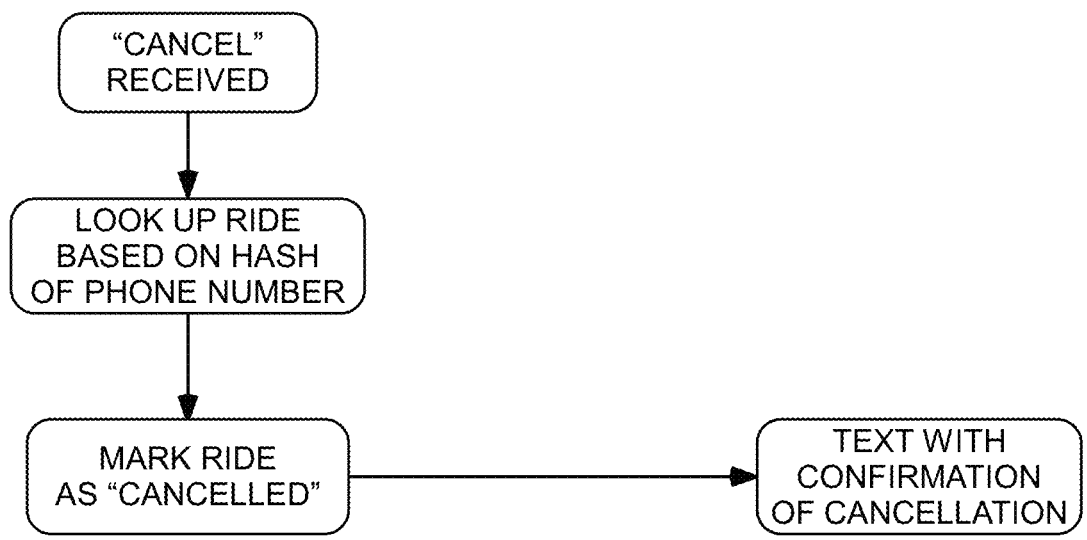
FIG. 5D is a flowchart of part of a ride coordination process according to an embodiment.
Figure 5E:
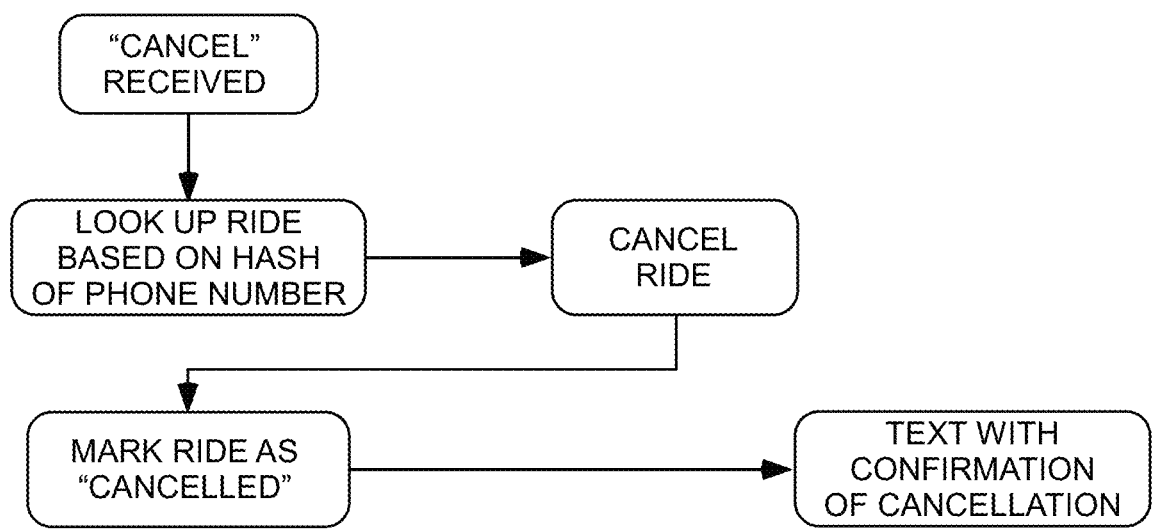
FIG. 5E is a flowchart of part of a ride coordination process according to an embodiment.
Figure 5F:
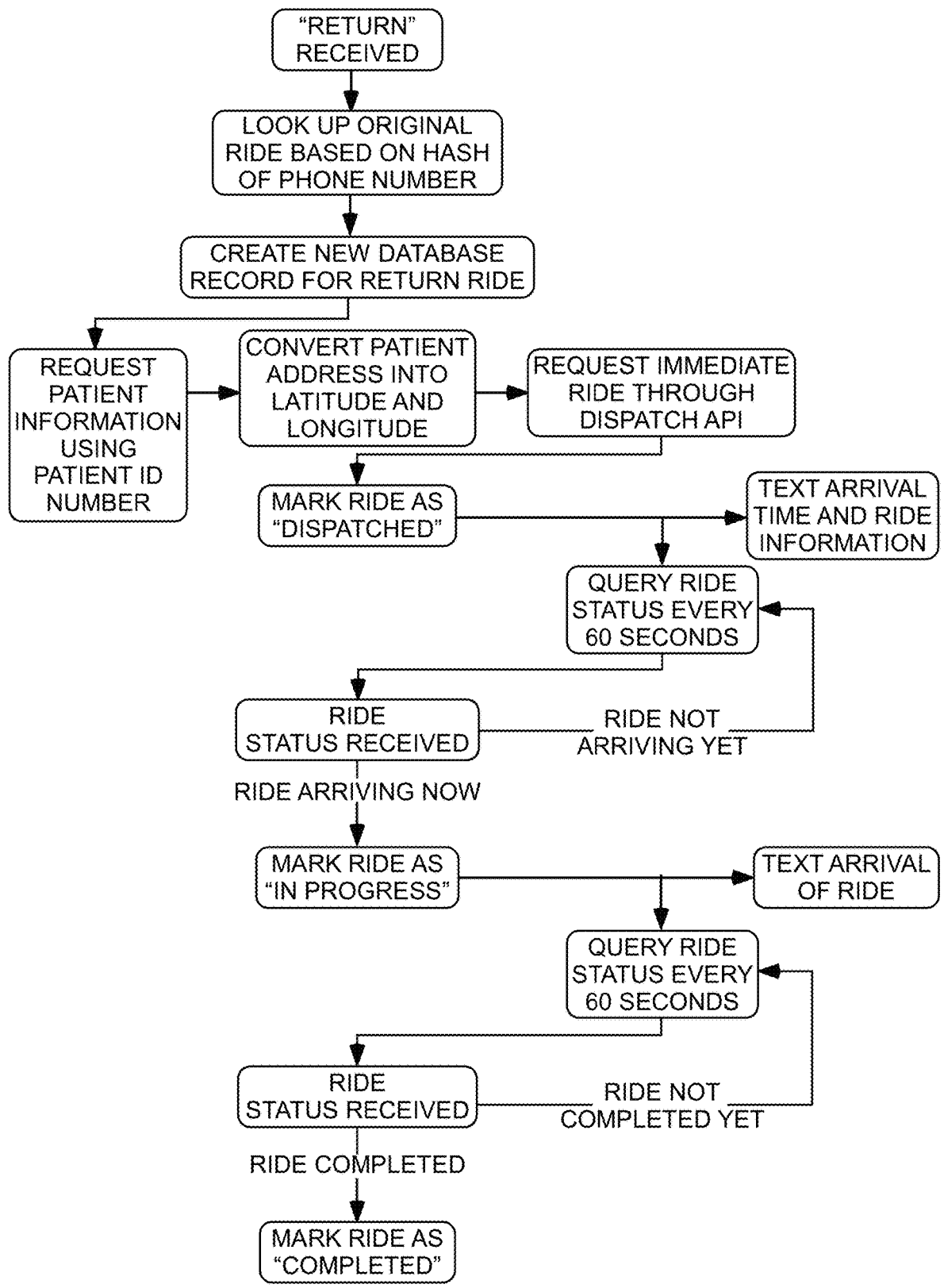
FIG. 5F is a flowchart of part of a ride coordination process according to an embodiment.

Referring to FIGS. 5D and 5E in particular, these flowcharts depict handling of patient appointment cancelations with system 100. FIG. 5D illustrates the tasks carried out by transportation coordination component 110 if it has been notified of a patient appointment, the patient initially responded affirmatively to the text message asking whether the patient would like a ride to the appointment, and the appointment or ride is canceled before transportation coordination component 110 has requested or scheduled it with transportation service 130. FIG. 5E illustrates the tasks carried out by transportation coordination component 110 if it has been notified of a patient appointment, the patient initially responded affirmatively to the text message asking whether the patient would like a ride to the appointment, and the appointment or ride is canceled after transportation coordination component 110 has requested or scheduled it with transportation service 130. Thus, the process of FIG. 5E requires the additional task of canceling a scheduled ride with transportation service 130 by transportation coordination component 110.

In some embodiments, information about appointment scheduling, cancelations and other updates can be communicated between EMR/EHR system 120 and transportation coordination component 110 in batches, such as hourly, daily or according to some other interval. This can provide more efficient operations in some embodiments and enable updates to both components to be made at convenient times (e.g., overnight, when there are fewer or no changes to appointments being made).

Figure 6:
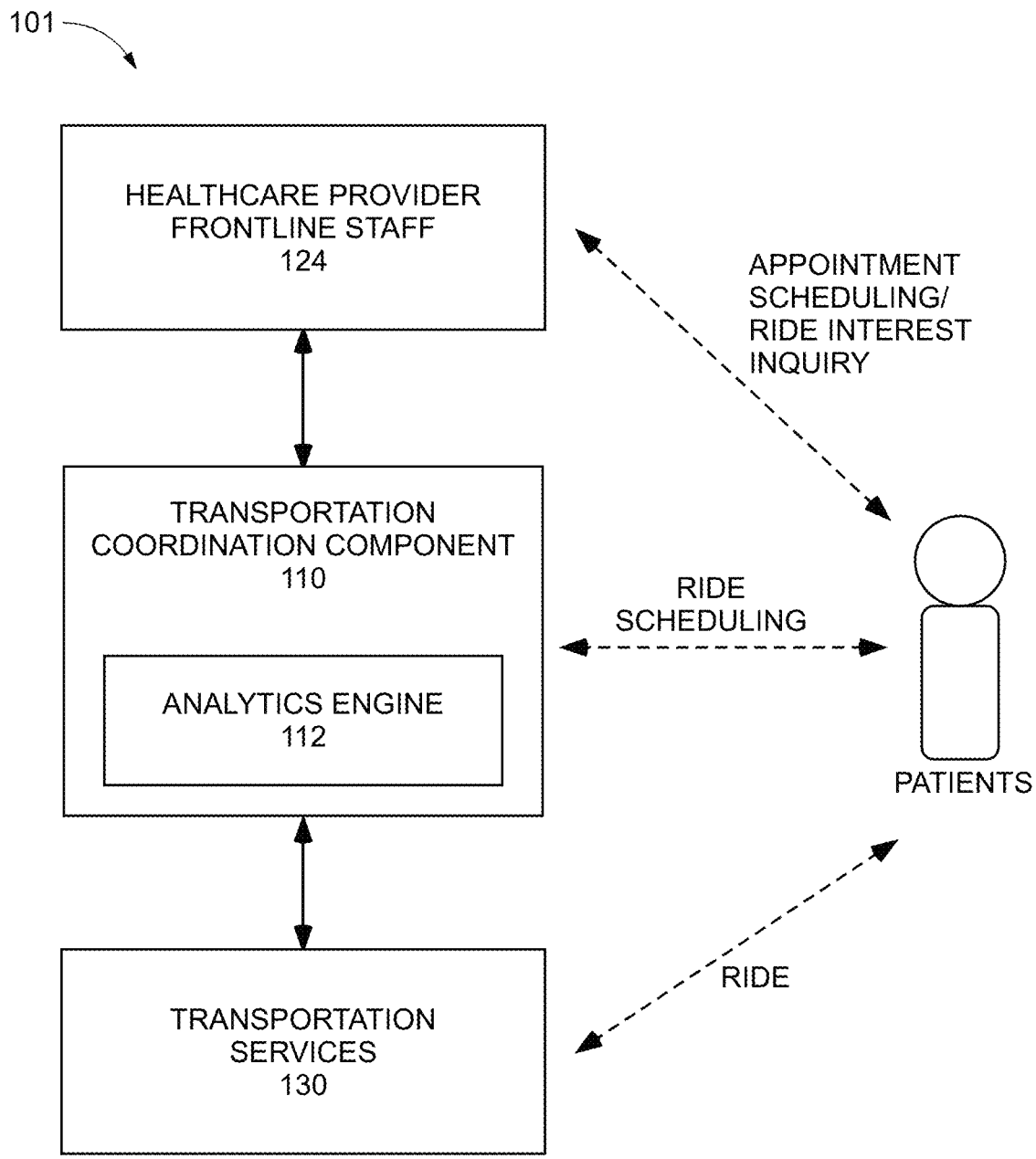
FIG. 6 is another block diagram of a healthcare transportation coordination system according to an embodiment.

Another embodiment of a system 101 similar to system 100 is depicted in FIG. 6. In system 101, transportation coordination component 110 interfaces with frontline staff 124 of the healthcare provider rather than with EMR/EHR system 120. In this embodiment, frontline staff 124 schedules an appointment for the patient and asks the patient if they would like a ride. If so, frontline staff 124 provides or initiates providing the relevant information to transportation coordination component 110. Frontline staff 124 can be the scheduling staff, or frontline staff 124 can additionally include a transport team to whom the patient is referred upon scheduling an appointment in order to arrange for transport by initiating a request to transportation coordination component 110. In some embodiments, it is the frontline staff (schedulers or transport team) that determines or confirms patient eligibility for transportation to and from appointments. In other embodiments, eligibility can be determined by transportation coordination component 110.

System 100 of FIGS. 1 and 2 also can comprise frontline staff involved in patient scheduling and a transport team involved in the scheduling and monitoring of patient transportation throughout the day. The scheduling and transport team do not need to be mutually exclusive and can overlap, according to the preferences of the particular healthcare provider in which they work.

Regardless of the configuration of system 100, healthcare provider 122 and/or frontline staff 124 can have access to a transportation "dashboard" that provides real-time, or near real-time, status information about rides scheduled, in progress and completed. FIGS. 7A-8F are examples of dashboards and dashboard content, but the particular arrangement, content and functionality of the dashboard can vary in other embodiments.

Figure 7A:
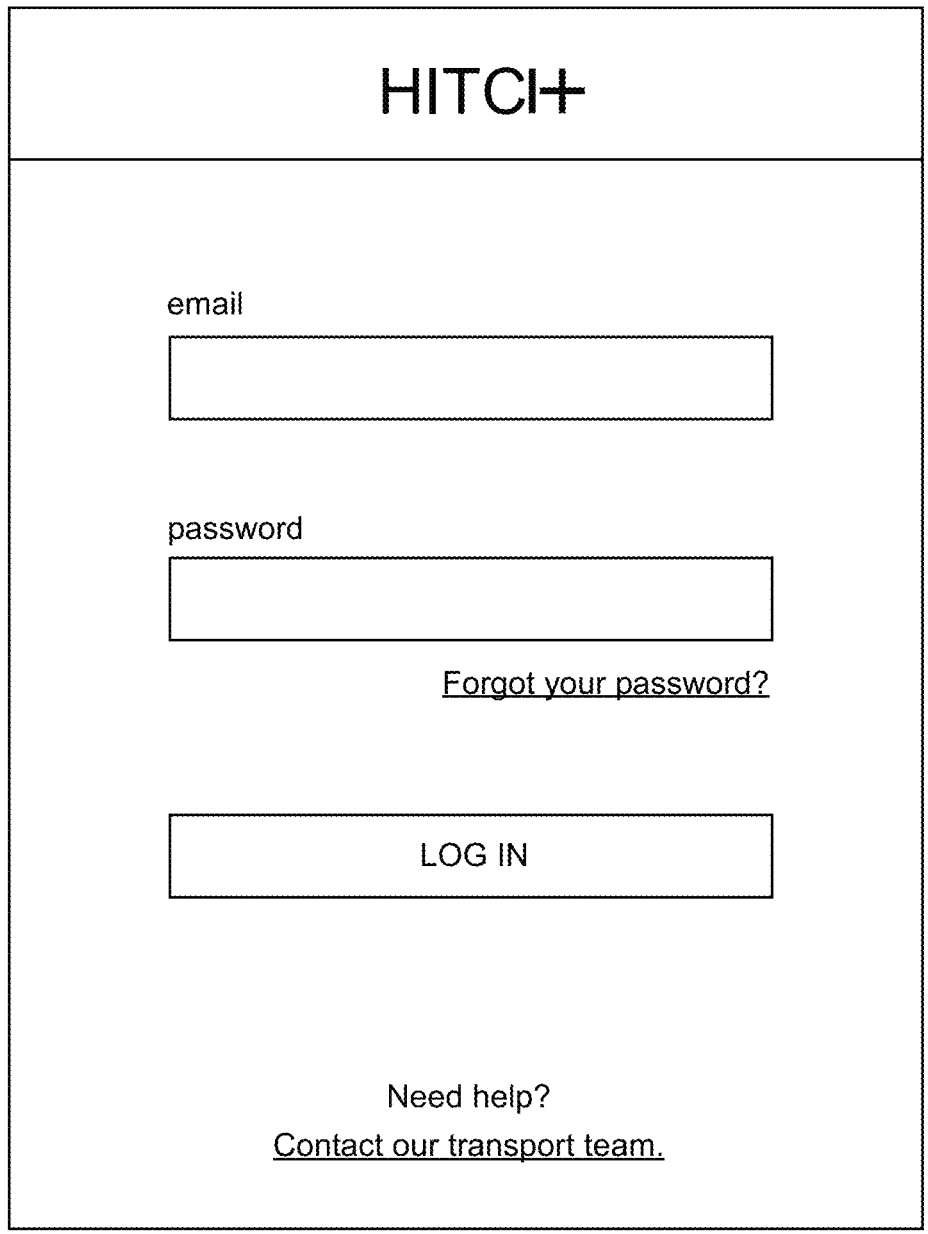
FIG. 7A is a screen-capture of a user interface of a healthcare transportation coordination system to a patient according to an embodiment.
Figure 7B:
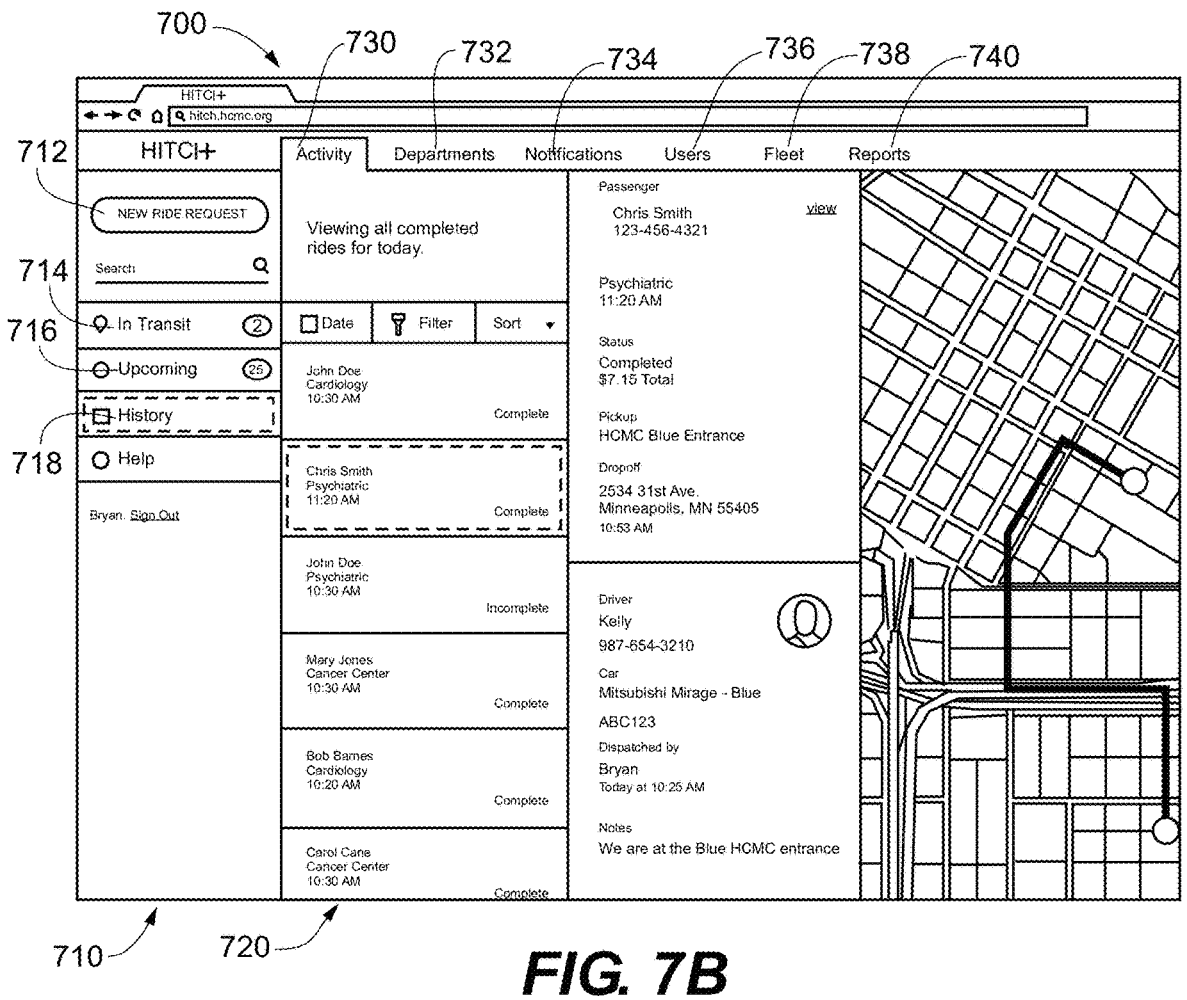
FIG. 7B is a screen-capture of a user interface of a healthcare transportation coordination system to a patient according to an embodiment.

After logging in (FIG. 7A), a user is presented with a healthcare provider-side user interface 700, such as the one depicted in FIG. 7B, that can be accessed by scheduling or other front-line staff of health care provider 122. User interface 700 comprises a navigation bar 710 and a main window 720.

Navigation bar 710 includes a "New Ride Request" button 712, via which a user can initiate a new ride request (such as in accordance with system 101 of FIG. 6, or in other situations in which manual requesting of a new ride is desired). Navigation bar 710 also includes navigation banners so that a user can view current rides in transit 714, upcoming rides 716 (i.e., those within some near-future time period, such as the 4, 8, 12 or 24 hours), and ride history 718. Ride history banner 718 is selected in FIG. 7B (along with the activity tab, discussed below) and shows both successfully completed rides and incomplete rides (i.e., those that were canceled late, for which the patient or driver did not show, etc.).

Various tabs, including an activity tab 730, departments tab 732, notifications tab 734, users tab 736, fleet tab 738, and reports tab 740, can be accessed and displayed in main window 720. Activity tab 730, along with history banner 718, is selected in the view depicted in FIG. 7B. The banner and tab arrangement enables users to select various types, combinations, and views of data related to the rides scheduled, taking place, and completed for their organization. In one embodiment, the navigation banners vary according to the selected tab, or the available tabs vary according to the selected navigation banner.

Figure 7C:
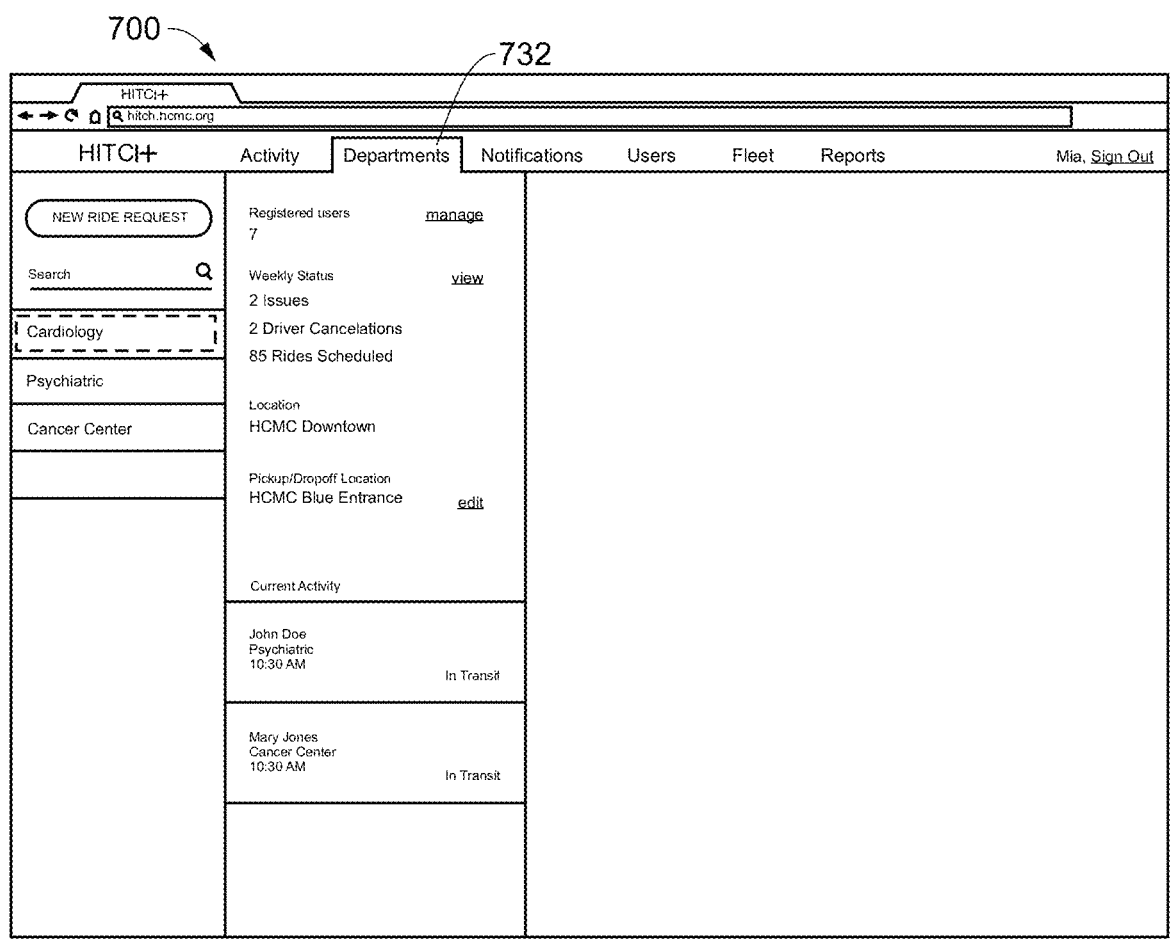
FIG. 7C is a screen-capture of a user interface of a healthcare transportation coordination system to a patient according to an embodiment.

For example, in FIG. 7C departments tab 732 is selected, and the banners in navigation bar 710 change to show the particular departments available or using the ride coordination features of transportation coordination component 110. In departments tab 732, a user can view weekly status or statistics along with current activity, in one embodiment. In some embodiments, users can customize one or more of the tabs, banners or information displayed in one or both. For example, instead of weekly status a user may wish to see daily or monthly status, and instead of current activity a user may wish to view successful rides completed by doctor or other medical professional. In other embodiments, the views are preselected by the institution (e.g., healthcare provider 122) or transportation coordination component 110.

Figure 7D:
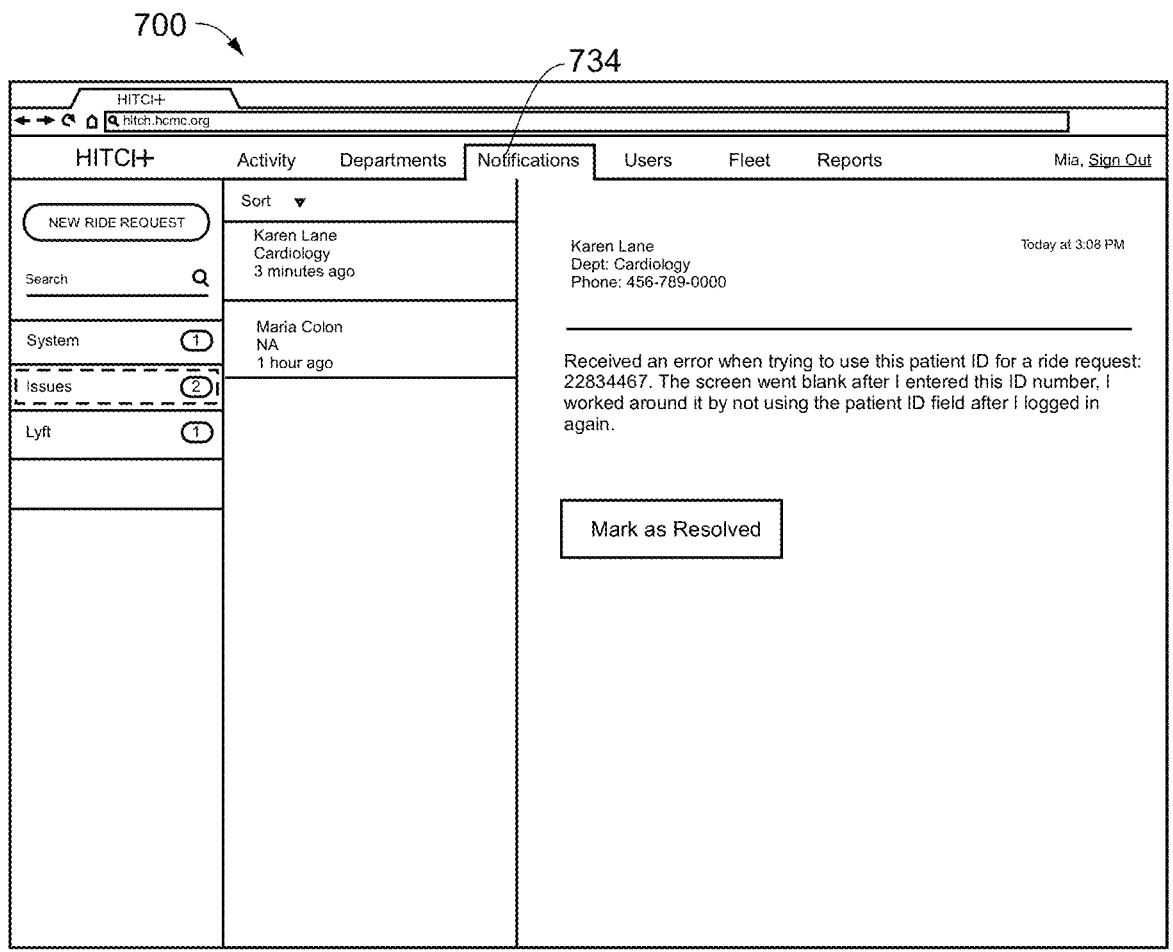
FIG. 7D is a screen-capture of a user interface of a healthcare transportation coordination system to a patient according to an embodiment.

FIG. 7D shows notification tab 734 selected in user interface 700. Notification tab 734 can display various errors or other issues that occurred and/or need resolution. Displaying the issues in a single tab can provide an easy way for a user to identify them and attend to them. In one embodiment, a user receives a notification (e.g., a pop-up window, a sound, a text message, automatic navigation to notification tab 734) whenever a new error or issue occurs. In another embodiment, these notifications are provided only for particular errors, such as those requiring immediate attention or action to address and/or resolve.

Figure 7E:
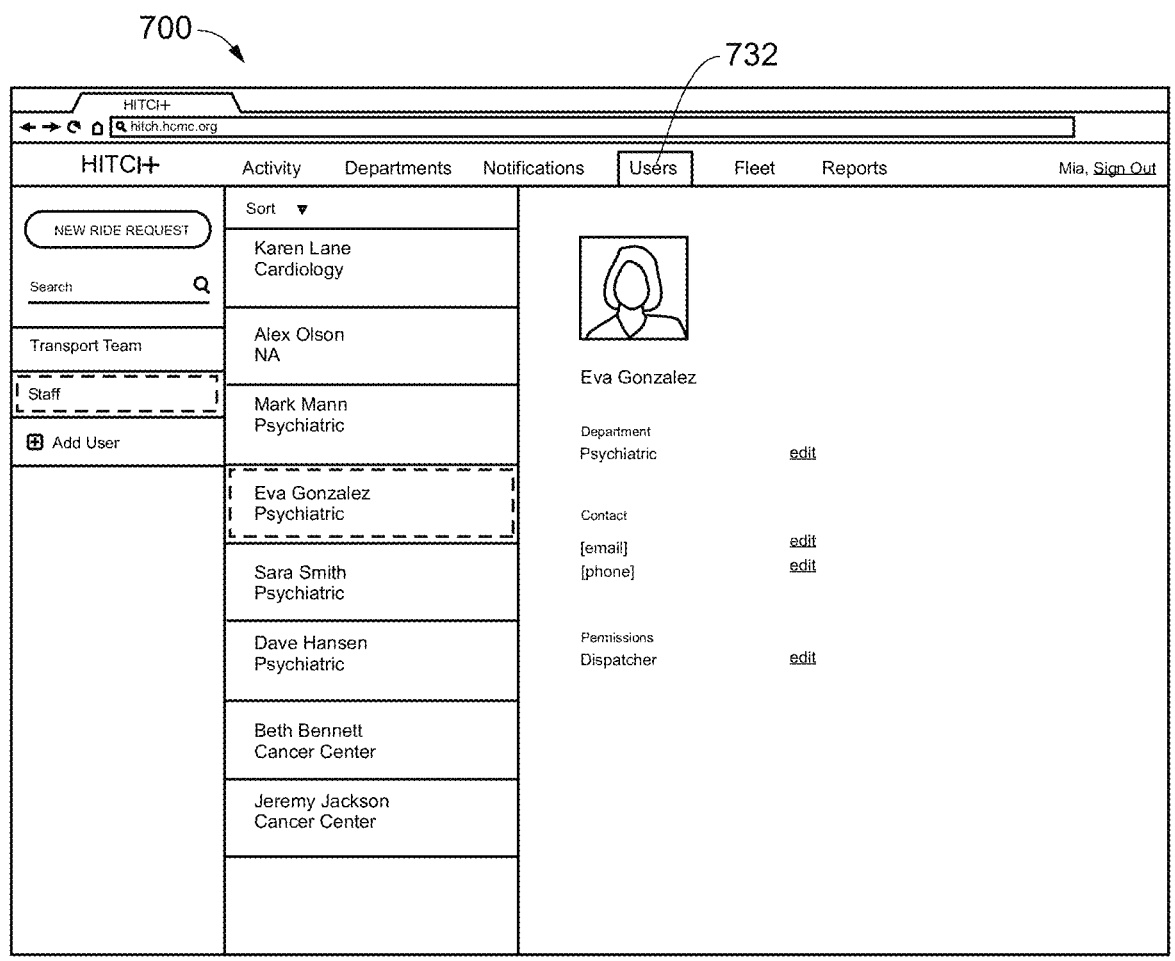
FIG. 7E is a screen-capture of a user interface of a healthcare transportation coordination system to a patient according to an embodiment.

FIG. 7E displays the users tab 736 in main window 720 of user interface 700. Users tab 736 can display information about internal systems users, such as frontline staff and the transport team, if applicable. This can be a convenient way for one user to identify another user who may be able to provide assistance, answer questions or otherwise advise regarding user of user interface 700 or transportation coordination component 110 more generally.

Figure 7F:
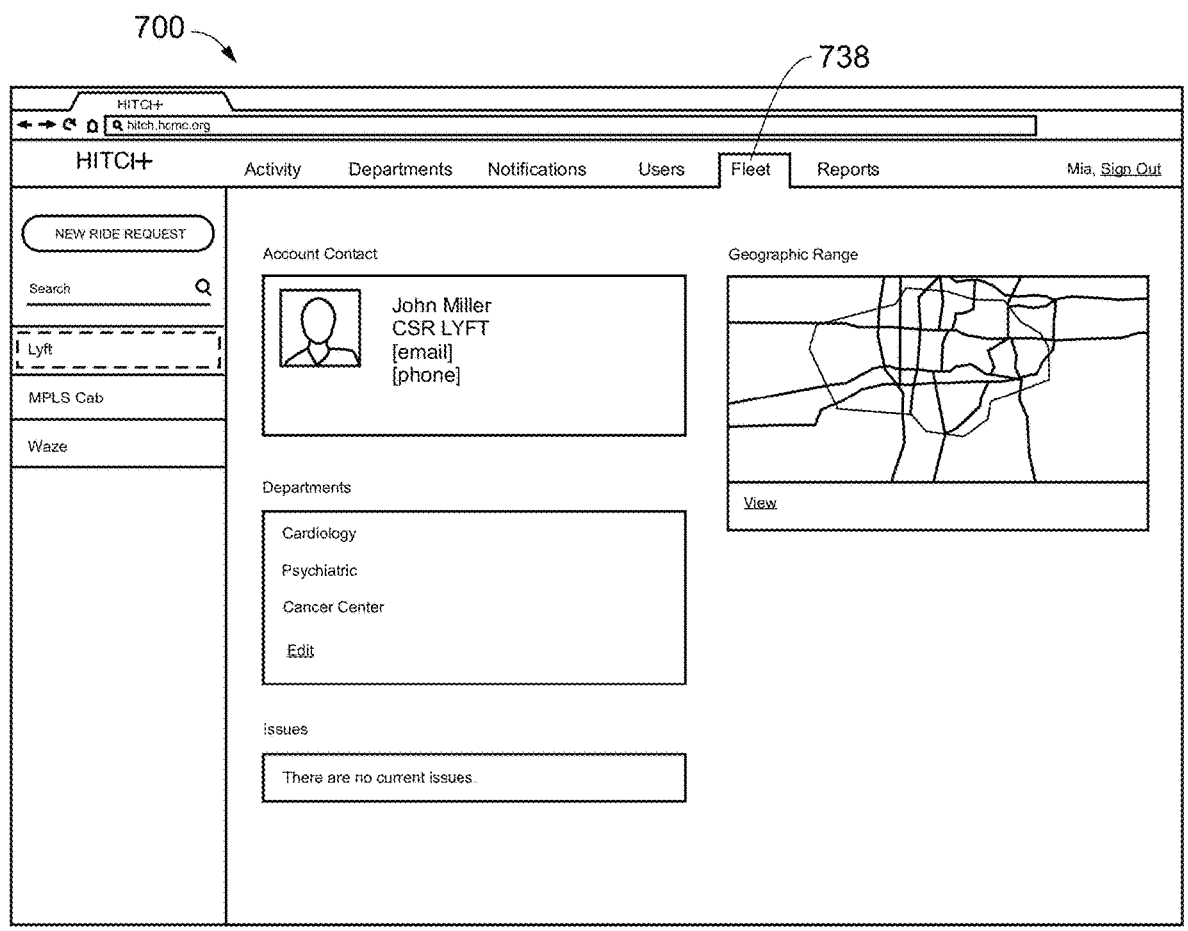
FIG. 7F is a screen-capture of a user interface of a healthcare transportation coordination system to a patient according to an embodiment.

Fleet tab 738 can provide information about transportation providers 130. This is shown in FIG. 7F. This information can enable a frontline staff user to contact a particular driver if there are questions about a particular ride and view the driver's history in case there is a pattern that needs addressing (e.g., repeated no-shows, negative feedback from patients).

Figure 8E:
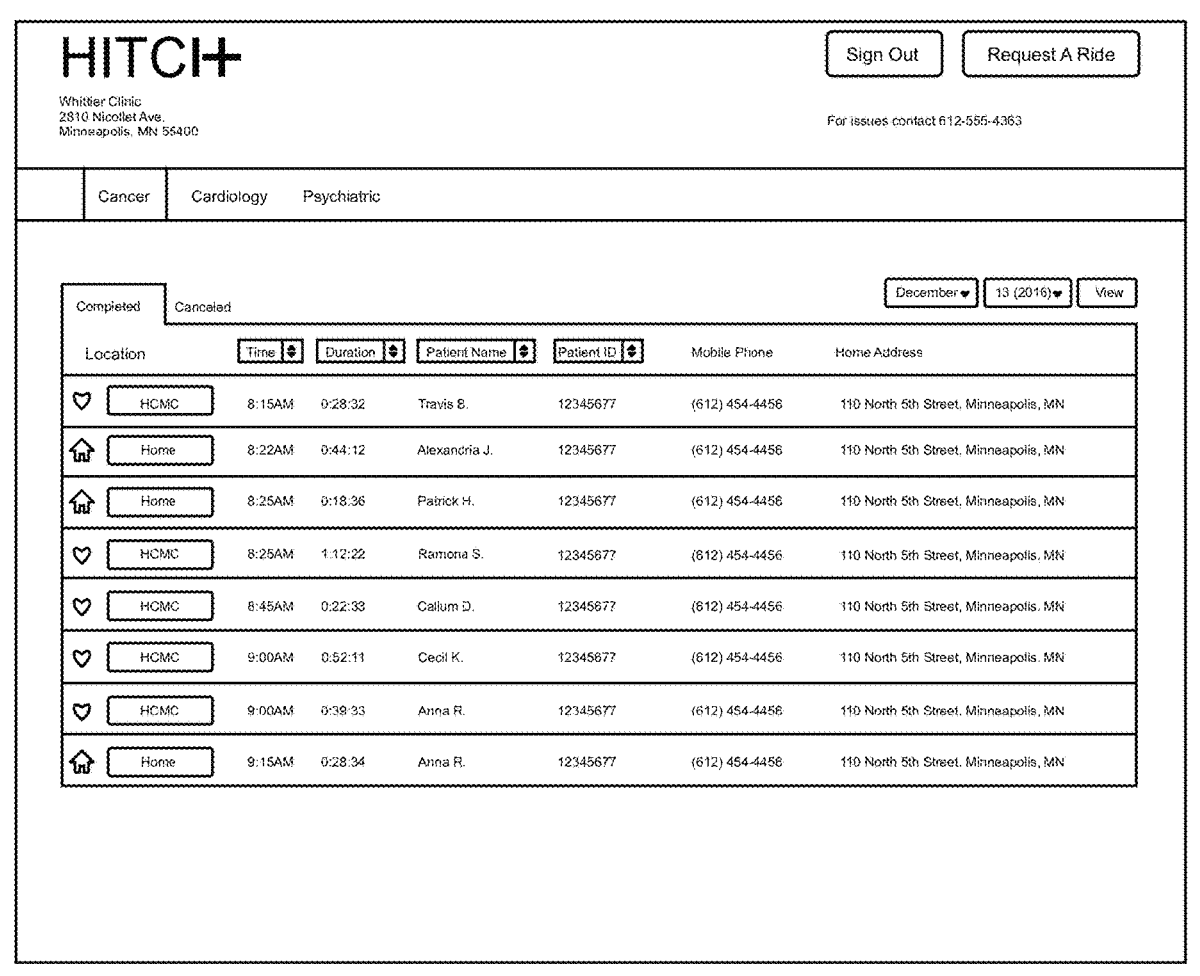

Another embodiment of a user interface 800 is depicted in FIGS. 8A-8F. User interface 800 is similar to user interface 700 but presents a different layout that may be preferred by some users. Information is sorted into several tabs, including arrivals 810 (FIG. 8A), departures 820 (FIG. 8B), completed 754 (FIG. 8C) and canceled 756 (FIG. 8D). FIG. 8E shows a historical completed tab view, in which a user can select a particular date to view completed (or canceled) rides on that day.

User interface 800 also includes a "Request a Ride" button, by which a frontline staff user can immediately request a ride for a patient. Selecting this button can cause the view of user interface 800 shown in FIG. 8F to be displayed. This can be useful if a patient needs or is able to take a same-day appointment or if staff become aware of another issue, such as a patient needing additional care at another facility after completing a first appointment. This button also can be helpful for staff to arrange return rides for patients that might have misunderstood, missed, or initially declined the return ride offer texted to them. Alternatively, in some embodiments frontline staff or a transport team may be responsible for coordinating and requesting all rides as they are needed, as previously discussed and in contrast with embodiments in which transportation coordination component 110 interfaces directly with EMR/EHR system 120 to coordinate rides with scheduled appointments. In these embodiments, user interface 800 (or 700) can be used as a dispatch tool for requesting and managing rides manually by frontline staff or a transport team.

Yet another embodiment of a user interface is depicted in FIGS. 9A-9I. This user interface is similar to user interfaces 700 and 800 but presents a different layout that may be preferred by some users.

Figure 9B:
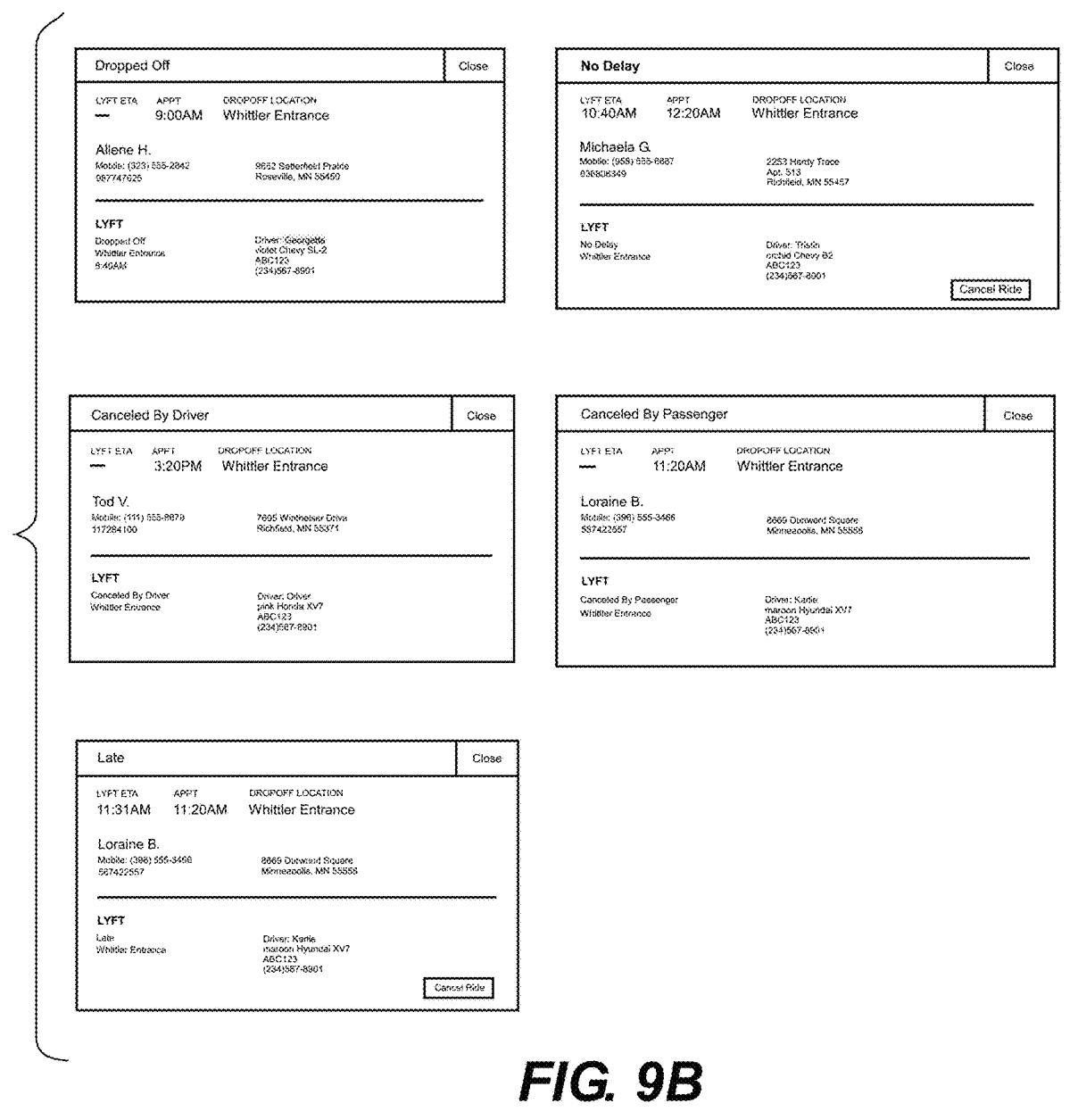

For example, FIG. 9A shows an arrival interface 902, which identifies the rides scheduled to arrive at a facility on a particular day, their time, and their status. By selecting any particular appointment or time, a healthcare provider or other user can get more detailed status information, such as is shown in FIG. 9B. This more detailed status information can include progress information and updates.

FIG. 9C shows a departure screen 904 of rides departing a facility on a particular day. Here, too, by selecting any particular appointment or time a healthcare provider or other user can get more detailed status information, similar to as is shown in FIG. 9B.

Figure 9D:
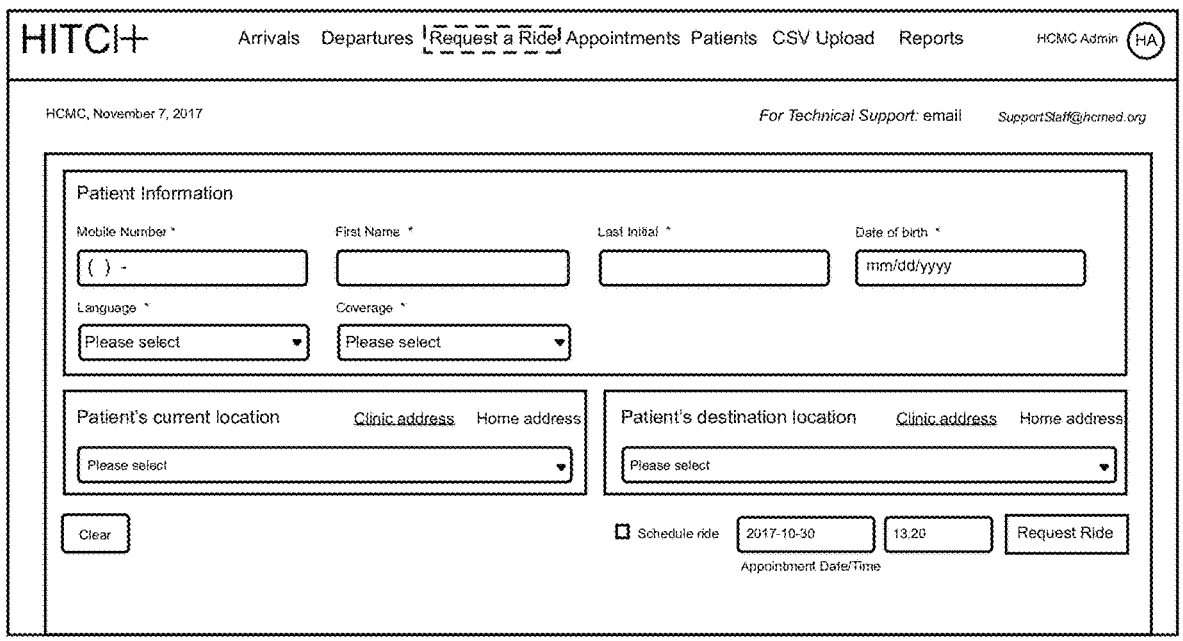
FIG. 9D is a screen-capture of a user interface of a healthcare transportation coordination system to a patient according to an embodiment.

FIG. 9D depicts a ride request screen 906. By completing the fields in screen 906, a healthcare provider or other user can arrange for a new ride for a patient.

Figures 9F, 9G:
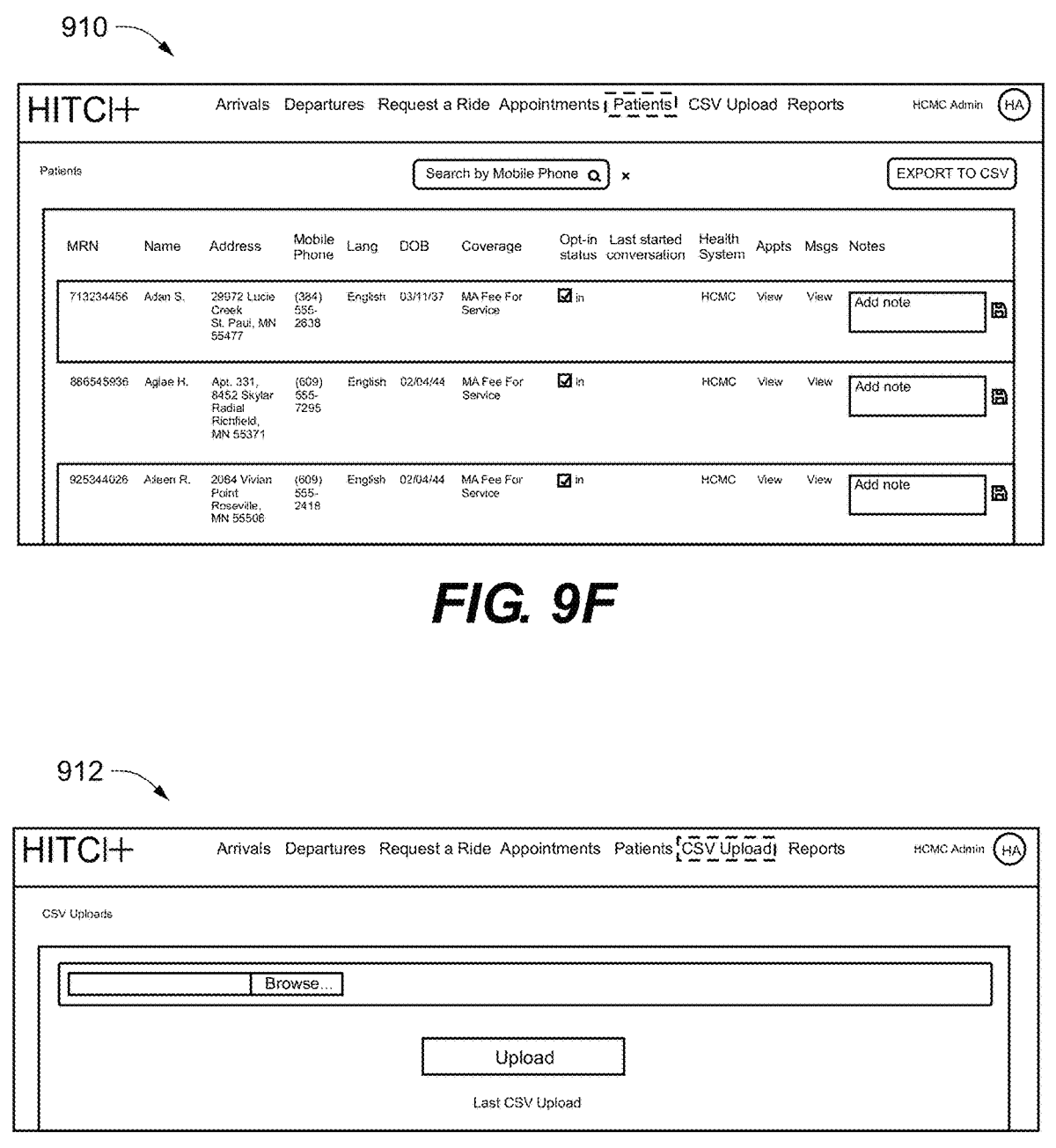

Additional screens present information about appointments (screen 908 in FIG. 9E) and patients (screen 910 in FIG. 9F). FIG. 9G is a comma separated value (CSV) file upload screen 912.

Figures 9H, 9I:
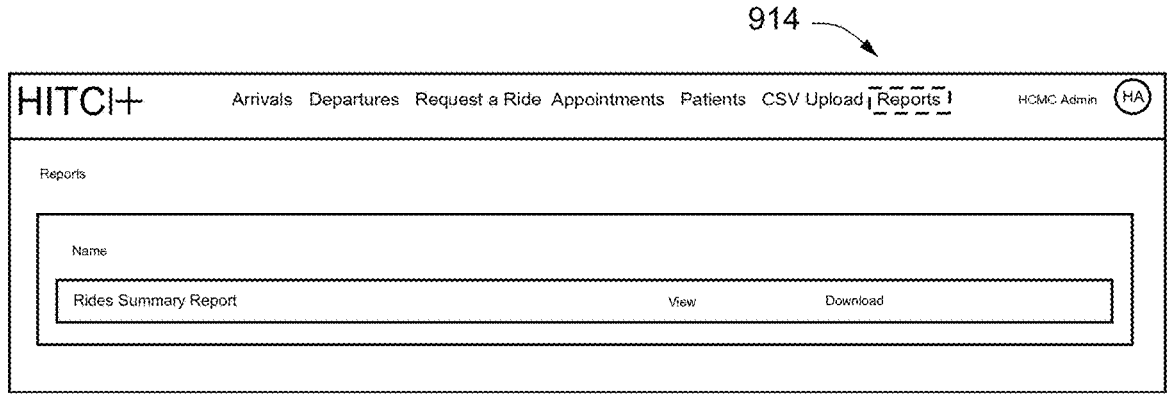
FIG. 9H is a screen-capture of a user interface of a healthcare transportation coordination system to a patient according to an embodiment.
FIG. 9I is a screen-capture of a user interface of a healthcare transportation coordination system to a patient according to an embodiment.

System 100 also can generate a variety of reports from a reports screen 914 depicted in FIG. 9H, and an example ride summary report screen 916 is depicted in FIG. 9I. The report data 918 is hyperlinked, such that a user can get more detailed information for any category (e.g., number of rides offered, number of denied offers) by clicking on the hyperlink.

Still other embodiments of user interfaces can be provided in other embodiments. As previously discussed, in some embodiments the features and functions of transportation coordination component 110 used or viewed by healthcare facility frontline staff can be integrated with (or at least appear integrated with) EMR/EHR system 120 or some other tool routinely used by that staff in their day-to-day tasks. Thus, the user interface can be integrated, appear integrated, comprise a stand-alone or separately accessed app (application program interface, API) or program, have its own web interface, be usable on a separate device (e.g., a tablet), or presented in some other way that provides the access and functionality desired by the healthcare organization and its staff.

Embodiments and examples discussed herein so far generally relate to arranging rides for patients to travel to and attend pre-scheduled medical appointments. The applications for and uses of system 100, in particular transportation coordination component 110, are much broader, however. For example, in some embodiments transportation coordination component 110 can arrange for other types of transportation and patient needs, such as scheduling home visits and house calls by doctors, nurses, social workers, health aides and others. In another embodiment, transportation coordination component 110 can schedule or interface with telemedicine systems, such that pre-appointment information can be collected or after-care remote check-ups completed. Still other applications and uses of telemedicine can be used with system 100 in various embodiments.

In some embodiments, analytics engine 112 can have a key role in managing various aspects of system 100. As previously discussed, analytics engine 112 can assist in determining when appointments should be scheduled (both to increase rates of patients showing up and also to avoid surge pricing and more expensive/less traffic-intense times of day). This can be done patient by patient (i.e., by analytics engine 112 filtering and analyzing past data for a particular patient), location by location (i.e., by analytics engine 112 mining data and identifying trends affecting a particular facility or location) or system-wide. For example, analytics engine 112 may filter and data mine data to identify demographic similarities between some patients, facilities or according to other characteristics and use those identified similarities to predict future behaviors. In particular, analytics engine 112 may determine that patients under the age of 30 in large metropolitan areas have a high no-show rate for appointments before 10 am. Therefore, analytics engine 112 will suggest scheduling these patients at 10:30 am or later. Analytics engine 112 may also determine that rideshare service drivers for a particular facility have a higher no-show rate before 9 am, between noon-1 pm, and after 4 pm. In another example, analytics engine 112 may identify a high no-show rate for a particular patient. Instead of continuing to try to schedule an out-of-home appointment for that patient, analytics engine 112 can suggest (e.g., to the patient's care team via system 100) that a mobile clinic or other in-home care team be scheduled and sent to the patient. Therefore, ride scheduling for those drivers at that facility will be scheduled to avoid those times. Various other trends and patterns can be identified by analytics engine 112 and taken into consideration as predictive analytics at all levels and points within system 100, with the goals of best meeting patient needs while also managing health care system and transportation needs efficiently. Using one or more of filtering, data mining, predictive analytics and machine learning makes analytics engine 112 an intelligent and powerful component of system 100, and also make it suitable for a variety of other uses and applications (discussed below).

While many embodiments discussed herein relate to a "middleware" arrangement of transportation coordination component 110, this need not be the case in all embodiments. For example, transportation coordination component 110 can be integrated with one or more of EMR/EHR system 120, healthcare provider 122, a health insurer, health maintenance organization (HMO), managed care organization, transportation provider 130 in various embodiments. In one particular example, an integrated EMR and insurance/health plan can additionally comprise some or all of the features and functions of transportation coordination component 110. These various embodiments of system 100 and/or transportation coordination component 110 can provide advantages to the various organizations and can be further adapted and customized for their needs.

Additionally, there are numerous applications of transportation coordination component 110 in industries other than healthcare. For example, embodiments of transportation coordination component can be configured for use in travel, hospitality and other industries. Hotels may wish to use transportation coordination component 110 to arrange for rides for their customers from airports, and transportation coordination component 110 can be configured to track flight arrivals and departures, query customers about ride needs, and dispatch various types of transit (e.g., ride sharing, black car, limo, SUV, van, bus) in a timely manner.

Airlines may want to offer ground transportation for premium or other fliers, and analytics engine 112 of transportation component 110 can apply filters and other tools to identify these fliers and make arrangements for them. While in some situations these arrangements can be complimentary for certain high-value passengers, in other situations the ground transportation can be a fee-based add-on that can generate additional revenue for the airline or its partners. Restaurants, theaters, sports venues, and other entertainment venues and facilities also can use customized versions of transportation coordination component 110 to transport their customers to dinner reservations, games, shows and other events. Transportation coordination component 110 also can be used to coordinate several events in a period of time, such as picking up guests at their hotel to take them to a dinner reservation at restaurant, picking them up from the restaurant after dinner to take them to the theater, picking them up after the theater to take them to a cocktail bar, and finally transporting them back to their hotel from the cocktail bar. Instead of the user having to make all these transportation arrangements and determine suitable times, transportation coordination component 110 can interface with any or all of the hotel, reservation service (e.g., OpenTable), restaurant, theater, and cocktail bar, or transportation coordination component 110 can operate independently for a fee paid by the user. The filters and analytics provided by analytics engine 112 of transportation coordination component 110 are powerful tools that can create a seamless evening for a user, either at the user's request or upon request by one of the entities (restaurant, theater, etc.). In one embodiment, each venue or service can be linked to transportation coordination component 110 to provide need, status and progress information (e.g., if a customer has requested a ride after dinner, transportation coordination component 110 can suggest to the server via their order management or reservation system (e.g. OpenTable) that the check be delivered by a particular time, at which point the ride can be requested). Many other applications of transportation coordination component 110 also exist, with the examples given herein being non-exhaustive.

Numerous advantages are provided by embodiments of system 100. For example, system 100 gives medical facilities and other organizations the previously unavailable ability to coordinate transportation services automatically, quickly, and for volumes of patients not previously possible. System 100 also is uniquely positioned to obtain and filter information received from EMR/EHR systems in order to identify trends (patient-specific, facility-specific, and others) that make scheduling appointments and arranging related transportation more efficient and likely to result in increased kept appointments. Additionally, system 100 can simultaneously arrange for and manage a volume of transportation requests not possible by a human because of the quantity of requests and the amount and sources of information necessary to manage and complete the requests. Moreover, system 100 facilitates communications between entities not previously connected and not possible to connect because of privacy and other concerns.

In various embodiments, system 100 and/or its components or subsystems can include computing devices, microprocessors, modules and other computer or computing devices, which can be any programmable device that accepts digital data as input, is configured to process the input according to instructions or algorithms, and provides results as outputs. In an embodiment, computing and other such devices discussed herein can be, comprise, contain or be coupled to a central processing unit (CPU) configured to carry out the instructions of a computer program. Computing and other such devices discussed herein are therefore configured to perform basic arithmetical, logical, and input/output operations.

Computing and other devices discussed herein can include memory. Memory can comprise volatile or non-volatile memory as required by the coupled computing device or processor to not only provide space to execute the instructions or algorithms, but also to provide the space to store the instructions themselves. In embodiments, volatile memory can include random access memory (RAM), dynamic random access memory (DRAM), or static random access memory (SRAM), for example. In embodiments, non-volatile memory can include read-only memory, flash memory, ferroelectric RAM, hard disk, floppy disk, magnetic tape, or optical disc storage, for example. The foregoing lists in no way limit the type of memory that can be used, as these embodiments are given only by way of example and are not intended to limit the scope of the disclosure.

In embodiments, the system or components thereof can comprise or include various modules or engines, each of which is constructed, programmed, configured, or otherwise adapted to autonomously carry out a function or set of functions. The term "engine" as used herein is defined as a real-world device, component, or arrangement of components implemented using hardware, such as by an application specific integrated circuit (ASIC) or field-programmable gate array (FPGA), for example, or as a combination of hardware and software, such as by a microprocessor system and a set of program instructions that adapt the engine to implement the particular functionality, which (while being executed) transform the microprocessor system into a special-purpose device. An engine can also be implemented as a combination of the two, with certain functions facilitated by hardware alone, and other functions facilitated by a combination of hardware and software. In certain implementations, at least a portion, and in some cases, all, of an engine can be executed on the processor(s) of one or more computing platforms that are made up of hardware (e.g., one or more processors, data storage devices such as memory or drive storage, input/output facilities such as network interface devices, video devices, keyboard, mouse or touchscreen devices, etc.) that execute an operating system, system programs, and application programs, while also implementing the engine using multitasking, multithreading, distributed (e.g., cluster, peer-peer, cloud, etc.) processing where appropriate, or other such techniques. Accordingly, each engine can be realized in a variety of physically realizable configurations, and should generally not be limited to any particular implementation exemplified herein, unless such limitations are expressly called out. In addition, an engine can itself be composed of more than one sub-engines, each of which can be regarded as an engine in its own right. Moreover, in the embodiments described herein, each of the various engines corresponds to a defined autonomous functionality; however, it should be understood that in other contemplated embodiments, each functionality can be distributed to more than one engine. Likewise, in other contemplated embodiments, multiple defined functionalities may be implemented by a single engine that performs those multiple functions, possibly alongside other functions, or distributed differently among a set of engines than specifically illustrated in the examples herein.

The content accessed by and/or underlying the applications and other components of system 100 can reside in one or more databases. A database is a structured set of data held in a computer. Database software provides functionalities that allow building, modifying, accessing, and updating both databases and the underlying data. Databases and database software reside on database servers. Database servers are collections of hardware and software that provide storage and access to the database and enable execution of the database software.

As an example, one or more databases accessed by or relied upon by various components of system 100 may be present on a single computing device in an embodiment. In other embodiments, one or more databases may be present on one or more database systems physically separate from one another. Similarly, one or more servers accessed or relied upon by various components of system 100 may comprise a single server device in an embodiment. In other embodiments, one or more servers may comprise one or more server systems physically separate from one another.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A method of coordinating transportation comprising:
providing a transportation coordination engine operably coupled to a plurality of communications channels and configured to communicate electronically over at least one of the plurality of communications channels with an electronic health record system server, at least one transportation service, and at least one patient electronic device;
linking the at least one patient electronic device with a particular patient;
generating a first queue based on at least one healthcare appointment and according to an appointment time and a healthcare provider resource;
generating a second queue for the at least one patient electronic device between at least one patient location and at least one healthcare facility, wherein the second queue processes communication with the at least one patient electronic device according to a patient location provided from the electronic health record system server and a time of a request of the at least one transportation service;
receiving, with the transportation coordination engine over at least one of the plurality of communications channels, from the electronic health record system server, an electronic communication of a healthcare appointment for a patient, the electronic communication comprising patient information and healthcare appointment information, the patient information comprising contact information;
assigning the healthcare appointment to a position in the first queue;
processing the first queue to trigger, with the transportation coordination engine, an electronic message to the at least one patient electronic device over the at least one communications channel based on the contact information, the electronic message comprising patient information, healthcare appointment information and a transportation query;
upon receiving a response to the transportation query, with the transportation coordination engine, assigning the at least one patient electronic device linked with the patient corresponding to the healthcare appointment to a first position in the second queue;
processing the second queue, with the transportation coordination engine, to coordinate transportation for the patient, the coordinating comprising determining a transportation initiation time, and ordering the transportation over at least one of the plurality of communications channels according to the transportation initiation time.

2. The method of claim 1, further comprising:
generating a third queue for the at least one patient electronic device between the at least one healthcare facility and the at least one patient location, wherein the third queue processes communication with the at least one patient electronic device according to a real-time status of a healthcare appointment;
monitoring a real-time status of the healthcare appointment based on information from the electronic health record system server;
assigning the at least one patient electronic device linked with the patient corresponding to the healthcare appointment to a position in the third queue based on the monitoring; and
processing the third queue, with the transportation coordination engine, to trigger an electronic message to the at least one patient electronic device linked with the patient corresponding to the healthcare appointment, the electronic message comprising a return trip transportation query, and upon receiving a response to the return trip transportation query, coordinating, with the transportation coordination engine, return trip transportation for the patient from a healthcare facility with at least one transportation service, the coordinating comprising determining a return trip transportation initiation time, and ordering the return trip transportation over the at least one communications channel according to the return trip transportation initiation time.

3. The method of claim 1, further comprising sending an electronic message to the at least one patient electronic device upon ordering the transportation.

4. The method of claim 1, further comprising:
receiving a request from a patient to schedule a new healthcare appointment;
analyzing the stored data, information received from an electronic health record of the patient, and healthcare appointment availability information; and
providing a suggested healthcare appointment time based on the analyzing.

5. The method of claim 4, wherein the analyzing comprises filtering at least one of the stored data or the information received from the electronic health record of the patient according to a criterion.

6. The method of claim 5, wherein the analyzing comprises:
selecting the criterion from the electronic health record of the patient;
filtering the stored data according to the selected criterion; and
identifying at least one trend in the filtered stored data.

7. The method of claim 1, further comprising updating the electronic health record system server based on the monitoring.

8. The method of claim 1, wherein the monitoring comprises providing real time progress information to the electronic health record system server.

9. The method of claim 1, wherein the electronic message to the at least one patient electronic device is an SMS message, wherein the at least one communications channel is a cellular network, and the contact information is a phone number of the at least one patient electronic device to be accessed over the cellular network, and wherein the response to the transportation query is an SMS message sent over the cellular network.

10. The method of claim 1, wherein the electronic communication indicating that a patient has scheduled a healthcare appointment is generated by:
determining an unfilled appointment slot based on a provider resource; and
suggesting the healthcare appointment for the unfilled appointment slot.

11. The method of claim 1, wherein the transportation is an autonomous or self-driving vehicle service.

12. A transportation coordination system configured to communicate electronically over at least one communications channel with an electronic health record system server, at least one transportation service, and at least one patient electronic device, the system comprising:
a processor and a memory, the processor configured to:
link the at least one patient electronic device with a particular patient;
generate a first queue for at least one healthcare appointment based on electronic health record system server data, wherein the first queue processes the at least one healthcare appointment according to an appointment time and a healthcare provider resource;
generate a second queue for the at least one patient electronic device between at least one patient location and at least one healthcare facility, wherein the second queue processes communication with each of the at least one patient electronic device according to a patient location provided from the electronic health record system server and a time of a request of the at least one transportation service;
receive, with the transportation coordination engine over the at least one communications channel, from the electronic health record system server, an electronic communication of a healthcare appointment for a patient, the electronic communication comprising patient information and healthcare appointment information, the patient information comprising contact information;
assign the healthcare appointment to a position in the first queue;
process the first queue to trigger, with the transportation coordination engine, an electronic message to the at least one patient electronic device over the at least one communications channel based on the contact information, the electronic message comprising patient information, healthcare appointment information and a transportation query;
upon receiving a response to the transportation query, with the transportation coordination engine, assigning the at least one patient electronic device linked with the patient corresponding to the healthcare appointment to a first position in the second queue;
process the second queue, with the transportation coordination engine, to coordinate transportation for the patient, the coordinating comprising determining a transportation initiation time, and ordering the transportation over the at least one communications channel according to the transportation initiation time.

13. The system of claim 12, wherein the processor is further configured to:
generate a third queue for the at least one patient electronic device between the at least one healthcare facility and the at least one patient location, wherein the third queue processes communication with each of the at least one patient electronic devices according to a real-time status of a healthcare appointment;
monitor a real-time status of the healthcare appointment based on information from the electronic health record system server;
assign the at least one patient electronic device linked with the patient corresponding to the healthcare appointment to a position in the third queue based on the monitoring; and
process the third queue, with the transportation coordination engine, to trigger an electronic message to the at least one patient electronic device linked with the patient corresponding to the healthcare appointment, the electronic message comprising a return trip transportation query, and upon receiving a response to the return trip transportation query, coordinating, with the transportation coordination engine, return trip transportation for the patient from a healthcare facility with at least one transportation service, the coordinating comprising determining a return trip transportation initiation time, and ordering the return trip transportation over the at least one communications channel according to the return trip transportation initiation time.

14. The system of claim 12, wherein the processor is further configured to send an electronic message to the at least one patient electronic device upon ordering the transportation.

15. The system of claim 12, wherein the processor is further configured to:
   receive a request from a patient to schedule a new healthcare appointment;
   analyze the stored data, information received from an electronic health record of the patient, and healthcare appointment availability information; and
   provide a suggested healthcare appointment time based on the analyzing.

16. The system of claim 15, wherein the processor is further configured to filter at least one of the stored data or the information received from the electronic health record of the patient according to a criterion.

17. The system of claim 16, wherein the processor is configured to analyze by:
   selecting the criterion from the electronic health record of the patient;
   filtering the stored data according to the selected criterion; and
   identifying at least one trend in the filtered stored data.

18. The system of claim 12, wherein the processor is further configured to update the electronic health record system server based on the monitoring.

19. The system of claim 12, wherein the monitoring comprises providing real time progress information to the electronic health record system server.

20. System of claim 12, wherein the electronic message to the at least one patient electronic device is an SMS message, wherein the at least one communications channel is a cellular network, and the contact information is a phone number of the at least one patient electronic device to be accessed over the cellular network, and wherein the response to the transportation query is an SMS message sent over the cellular network.

21. The system of claim 12, wherein the electronic communication indicating that a patient has scheduled a healthcare appointment is generated by:
   determining an unfilled appointment slot based on a provider resource; and
   suggesting the healthcare appointment for the unfilled appointment slot.

22. The system of claim 12, wherein the transportation is an autonomous or self-driving vehicle service.

* * * * *